United States Patent
Swanson

(10) Patent No.: US 7,776,033 B2
(45) Date of Patent: Aug. 17, 2010

(54) WETTABLE STRUCTURES INCLUDING CONDUCTIVE FIBERS AND APPARATUS INCLUDING THE SAME

(75) Inventor: David K. Swanson, Campbell, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1138 days.

(21) Appl. No.: 11/031,630

(22) Filed: Jan. 8, 2005

(65) Prior Publication Data
US 2006/0155273 A1    Jul. 13, 2006

(51) Int. Cl.
*A61B 18/14* (2006.01)
(52) U.S. Cl. .......................... 606/41; 606/51
(58) Field of Classification Search .............. 606/41; 600/397
See application file for complete search history.

(56) References Cited

U.S. PATENT DOCUMENTS

| | | | |
|---|---|---|---|
| 3,920,021 A | 11/1975 | Hiltebrandt | |
| 3,998,215 A * | 12/1976 | Anderson et al. | ........... 600/397 |
| 4,819,633 A | 4/1989 | Bauer et al. | |
| 4,834,090 A | 5/1989 | Moore | |
| 4,919,648 A * | 4/1990 | Sibalis | ............ 604/20 |
| 5,122,139 A | 6/1992 | Sutter | |
| 5,250,072 A | 10/1993 | Jain | |
| 5,443,463 A | 8/1995 | Stern | |
| 5,456,682 A | 10/1995 | Edwards et al. | |
| 5,582,609 A | 12/1996 | Swanson et al. | |
| 5,755,715 A | 5/1998 | Stern et al. | |
| 5,797,903 A * | 8/1998 | Swanson et al. | ............... 606/34 |
| 5,797,905 A | 8/1998 | Fleischman et al. | |
| 5,840,076 A | 11/1998 | Swanson | |
| 5,944,718 A | 8/1999 | Austin et al. | |
| 6,001,093 A | 12/1999 | Swanson | |
| 6,004,320 A | 12/1999 | Casscells et al. | |
| 6,010,500 A | 1/2000 | Sherman | |
| 6,010,516 A | 1/2000 | Hulka | |
| 6,013,052 A | 1/2000 | Durman et al. | |
| 6,032,077 A * | 2/2000 | Pomeranz | ................... 607/101 |
| 6,071,279 A | 6/2000 | Fleischman et al. | |
| 6,076,012 A | 6/2000 | Swanson et al. | |
| 6,096,033 A | 8/2000 | Tu et al. | |
| 6,142,994 A | 11/2000 | Swanson et al. | |
| 6,152,899 A | 11/2000 | Farley et al. | |
| 6,164,283 A | 12/2000 | Lesh | |
| 6,179,835 B1 | 1/2001 | Panescu et al. | |

(Continued)

FOREIGN PATENT DOCUMENTS

EP    0853922    7/1998

(Continued)

OTHER PUBLICATIONS

Office Action dated Mar. 3, 2005, for U.S. Appl. No. 10/079,944, filed Feb. 19, 2002, Inventor: Huy D. Phan (10 pages).

(Continued)

*Primary Examiner*—Lee S Cohen
(74) *Attorney, Agent, or Firm*—Vista IP Law Group LLP

(57) ABSTRACT

An apparatus including a wettable structure and a plurality of conductive fibers carried by the wettable structure.

29 Claims, 12 Drawing Sheets

U.S. PATENT DOCUMENTS

| | | | |
|---|---|---|---|
| 6,203,525 | B1 | 3/2001 | Whayne et al. |
| 6,214,002 | B1 | 4/2001 | Fleischman et al. |
| 6,237,605 | B1 | 5/2001 | Vaska et al. |
| 6,241,754 | B1 | 6/2001 | Swanson et al. |
| 6,245,064 | B1 | 6/2001 | Lesh et al. |
| 6,245,068 | B1 | 6/2001 | Olson et al. |
| 6,251,093 | B1 | 6/2001 | Valley et al. |
| 6,273,887 | B1 | 8/2001 | Yamauchi et al. |
| 6,277,117 | B1 | 8/2001 | Tetzlaff |
| 6,290,699 | B1 | 9/2001 | Hall et al. |
| 6,296,640 | B1 | 10/2001 | Wampler et al. |
| 6,312,426 | B1 | 11/2001 | Rittman, III et al. |
| 6,325,797 | B1 | 12/2001 | Stewart et al. |
| 6,391,024 | B1 | 5/2002 | Sun et al. |
| 6,425,895 | B1 | 7/2002 | Swanson et al. |
| 6,464,700 | B1 | 10/2002 | Koblish et al. |
| 6,488,680 | B1 | 12/2002 | Francischelli et al. |
| 6,511,480 | B1 | 1/2003 | Tetzlaff et al. |
| 6,522,930 | B1 | 2/2003 | Schaer et al. |
| 6,527,767 | B2 | 3/2003 | Wang et al. |
| 6,579,288 | B1 | 6/2003 | Swanson |
| 6,645,199 | B1 | 11/2003 | Jenkins et al. |
| 6,645,200 | B1 | 11/2003 | Koblish et al. |
| 6,663,622 | B1 | 12/2003 | Foley |
| 6,692,491 | B1 | 2/2004 | Phan |
| 6,780,180 | B1 * | 8/2004 | Goble et al. .................. 606/41 |
| 6,786,905 | B2 | 9/2004 | Swanson et al. |
| 6,887,238 | B2 | 5/2005 | Jahns |
| 6,896,673 | B2 | 5/2005 | Hooven |
| 6,926,712 | B2 | 8/2005 | Phan |
| 6,932,816 | B2 | 8/2005 | Phan |
| 6,939,350 | B2 | 9/2005 | Phan |
| 6,942,661 | B2 | 9/2005 | Swanson |
| 7,147,633 | B2 | 12/2006 | Chee et al. |
| 7,207,988 | B2 | 4/2007 | Leckrone |
| 7,250,048 | B2 | 7/2007 | Francischelli et al. |
| 7,288,088 | B2 | 10/2007 | Swanson |
| 7,326,206 | B2 * | 2/2008 | Paul et al. ..................... 606/41 |
| 7,371,233 | B2 | 5/2008 | Swanson et al. |
| 2002/0026187 | A1 | 2/2002 | Swanson |
| 2003/0014048 | A1 | 1/2003 | Swanson |
| 2003/0014049 | A1 * | 1/2003 | Koblish et al. ................ 606/41 |
| 2003/0069572 | A1 | 4/2003 | Wellman et al. |
| 2003/0120268 | A1 | 6/2003 | Bertolero et al. |
| 2003/0139644 | A1 | 7/2003 | Parsons et al. |
| 2003/0158547 | A1 | 8/2003 | Phan |
| 2004/0059325 | A1 | 3/2004 | Swanson |
| 2004/0087935 | A1 | 5/2004 | Taimisto |
| 2004/0186467 | A1 | 9/2004 | Swanson |
| 2005/0019653 | A1 | 1/2005 | Dahlberg |
| 2005/0113827 | A1 | 5/2005 | Dumbauld |
| 2005/0119654 | A1 | 6/2005 | Swanson et al. |
| 2005/0187544 | A1 | 8/2005 | Swanson |
| 2006/0047277 | A1 * | 3/2006 | Eberl et al. ................... 606/41 |
| 2006/0155274 | A1 | 7/2006 | Swanson |
| 2007/0198041 | A1 | 8/2007 | Rupp et al. |

FOREIGN PATENT DOCUMENTS

| | | |
|---|---|---|
| WO | WO 00/24330 | 5/2000 |
| WO | WO 00/29062 | 5/2000 |

OTHER PUBLICATIONS

Amendment dated Jul. 14, 2003, for U.S. Appl. No. 10/079,944, filed Feb. 19, 2002, Inventor: Huy D. Phan (18 pages).
Office Action dated Oct. 8, 2003, for U.S. Appl. No. 10/079,944, filed Feb. 19, 2002, Inventor: Huy D. Phan (7 pages).
Amendment dated Jan. 12, 2004, for U.S. Appl. No. 10/079,944, filed Feb. 19, 2002, Inventor: Huy D. Phan (13 pages).
Advisory Action dated Feb. 3, 2004, for U.S. Appl. No. 10/079,944, filed Feb. 19, 2002, Inventor: Huy D. Phan (3 pages).
Office Action dated Mar. 4, 2004, for U.S. Appl. No. 10/079,944, filed Feb. 19, 2002, Inventor: Huy D. Phan (6 pages).
Amendment dated May 14, 2004, for U.S. Appl. No. 10/079,944, filed Feb. 19, 2002, Inventor: Huy D. Phan (12 pages).
Office Action dated Oct. 4, 2004, for U.S. Appl. No. 10/079,944, filed Feb. 19, 2002, Inventor: Huy D. Phan (13 pages).
Amendment dated Dec. 9, 2004, for U.S. Appl. No. 10/079,944, filed Feb. 19, 2002, Inventor: Huy D. Phan (5 pages).
Notice of Allowance dated Jan. 18, 2005, for U.S. Appl. No. 10/079,944, filed Feb. 19, 2002, Inventor: Huy D. Phan (7 pages).
Office Action dated Mar. 27, 2007, for U.S. Appl. No. 11/067,391, filed Feb. 25, 2005, Inventor: Greg Eberl (5 pages).
Response dated Apr. 16, 2007, for U.S. Appl. No. 11/067,391, filed Feb. 25, 2005, Inventor: Greg Erberl (7 pages).
Office Action dated Jun. 28, 2007, for U.S. Appl. No. 11/067,391, filed Feb. 25, 2005, Inventor: Greg Eberl (12 pages).
Amendment dated Sep. 28, 2007, for U.S. Appl. No. 11/067,391, filed Feb. 25, 2005, Inventor: Greg Eberl (10 pages).
Office Action dated Dec. 28, 2007, for U.S. Appl. No. 11/067,391, filed Feb. 25, 2005, Inventor: Greg Eberl (9 pages).
Office Action dated Jul. 17, 2007, for U.S. Appl. No. 11/067,535, filed Feb. 25, 2005, Inventor: Greg Ebert (5 pages).
Response dated Aug. 17, 2007, for U.S. Appl. No. 11/067,535, filed Feb. 25, 2005, Inventor: Greg Ebert (7 pages).
Office Action dated Sep. 25, 2007, for U.S. Appl. No. 11/067,535, filed Feb. 25, 2005, Inventor: Greg Ebert (12 pages).
Amendment dated Jan. 25, 2008, for U.S. Appl. No. 11/067,535, filed Feb. 25, 2005, Inventor: Greg Ebert (10 pages).
PCT International Preliminary Examination Report for PCT/US2002/038092, Applicant: Scimed Life Systems, Inc., Forms PCT/IPEA/416 and PCT/IPEA/409, dated Mar. 12, 2004 (7 pages).
PCT International Preliminary Examination Report for PCT/US2002/038092, Applicant: Scimed Life Systems, Inc., Forms PCT/ISA/210 and PCT/ISA/220, dated Mar. 28, 2003 (7 pages).
PCT Written Opinion for PCT/US2002/038092, Applicant: Scimed Life Systems, Inc., Forms PCT/ISA/237, dated Nov. 13, 2003 (5 pages).
PCT International Search Report for PCT/US2005/045055, Applicant: Boston Scientific Scimed, Inc., Forms PCT/ISA/210, and PCT/ISA/220, dated Oct. 27, 2006 (10 pages).
Office Action dated Mar. 25, 2008 for related U.S. Appl. No. 11/031,631, filed Jan. 8, 2005, Inventor: David K. Swanson (6 pages).
Office Action dated Mar. 26, 2008 for related U.S. Appl. No. 11/031,629, filed Jan. 8, 2005, Inventor: David K. Swanson (16 pages).
Office Action dated May 28, 2008 for related U.S. Appl. No. 11/141,405, filed May 28, 2005, Inventor: David K. Swanson (7 pages).
Amendment dated Mar. 27, 2008 for related U.S. Appl. No. 11/067,391, filed Feb. 25, 2005, Inventor: Greg Eberl (11 pages).
Amendment dated Jun. 20, 2008 for related U.S. Appl. No. 11/031,631, filed Jan. 8, 2005, Inventor: David Swanson (19 pages).
Papers from file history for related U.S. Appl. No. 11/031,629, filed Jan. 8, 2005, Applicant Boston Scientific, including: Final Office Action for U.S. Appl. No. 11/031,629, dated Apr. 30, 2009, Amendment response to non final Office Action dated Nov. 14, 2008, for U.S. Appl. No. 11/031,629, response submitted Mar. 13, 2009, Non final Office Action for U.S. Appl. No. 11/031,629, dated Nov. 14, 2008, Amendment response to non final Office Action dated Mar. 26, 2008, for U.S. Appl. No. 11/031,629, response submitted Jun. 26, 2008, (69 pages).
Papers from filed history for related U.S. Appl. No. 11/067,535, filed Feb. 25, 2005, Applicant Boston Scientific, including: Final Office Action for U.S. Appl. No. 11/067,535, dated Mar. 13, 2009, (34 pages).
Papers from file history for related U.S. Appl. No. 11/031,631, filed Jan. 8, 2005, Applicant Boston Scientific, including: Non final Supplemental Office Action for U.S. Appl. No. 11/031,631, dated Mar. 9, 2009, Non final Office Action for U.S. Appl. No. 11/031,631, dated Feb. 24, 2009, Amendment response to non final Office Action dated Sep. 16, 2008, for U.S. Appl. No. 11/031,631, response submitted Jan. 16, 2009, Non final Office Action for U.S. Appl. No. 11/031,631, dated Sep. 16, 2008, Amendment response to non final Office Action dated Mar. 25, 2008, for U.S. Appl. No. 11/031,631, response submitted Jun. 20, 2008, (63 pages).
Papers from filed history for related U.S. Appl. No. 11/141,405, filed May 28, 2005, Applicant Boston Scientific, including: Amendment response to non final Office Action dated May 28, 2008, for U.S. Appl. No. 11/141,405, response submitted Sep. 15, 2008, (16 pages).
Amendment dated Mar. 27, 2008 in U.S. Appl. No. 11/067,391, (14 pages).
Office Action dated Aug. 21, 2009 in U.S. Appl. No. 11/031/631, (7 pages).
Amendment dated Jun. 3, 2009 in U.S. Appl. No. 11/031/631, (12 pages).
Amendment dated Sep. 9, 2009 in U.S. Appl. No. 11/141,405, (11 pages).
Office Action dated Jun. 9, 2009 in U.S. Appl. No. 11/141,405, (13 pages).
Amendment dated Aug. 13, 2009 in U.S. Appl. No. 11/067,535, (10 pages).
Office Action dated Aug. 6, 2009 in U.S. Appl. No. 11/031,629, (7 pages).
Amendment dated Jun. 30, 2009 in U.S. Appl. No. 11/031,629, (12 pages).
Office Action dated Nov. 20, 2009 in U.S. Appl. No. 11/067,391; Inventor: Greg Eberl; Filing Date: Feb. 25, 2005 (19 pages).
Amendment dated Jan. 12, 2010 in U.S. Appl. No. 11/067,391; Inventor: Greg Eberl; Filing Date: Feb. 25, 2005 (8 pages).
Amendment dated Jun. 3, 2009 in U.S. Appl. No. 11/031,631; Inventor: David K. Swanson, Filing Date: Jan. 8, 2005 (10 pages).
Office Action dated Aug. 21, 2009 in U.S. Appl. No. 11/031,631; Inventor: David K. Swanson, Filing Date: Jan. 8, 2005 (7 pages).
Amendment dated Dec. 21, 2009 in U.S. Appl. No. 11/031,631; Inventor: David K. Swanson, Filing Date: Jan. 8, 2005 (11 pages).
Office Action dated Jun. 9, 2009 in U.S. Appl. No. 11/141,405; Inventor: David K. Swanson, Filing Date: May 28, 2005 (13 pages).
Amendment dated Sep. 9, 2009 in U.S. Appl. No. 11/141,405; Inventor: David K. Swanson, Filing Date: May 28, 2005 (9 pages).
Office Action dated Dec. 28, 2009 in U.S. Appl. No. 11/141,405; Inventor: David K. Swanson, Filing Date: May 28, 2005 (11 pages).
Amendment dated Aug. 13, 2009 in U.S. Appl. No. 11/067,535; Inventor: Greg Eberl, Filing Date: Feb. 25, 2005 (7 pages).
Office Action dated Sep. 24, 2009 in U.S. Appl. No. 11/067,535; Inventor: Greg Eberl, Filing Date: Feb. 25, 2005 (11 pages).
Amendment dated Oct. 9, 2009 in U.S. Appl. No. 11/067,535; Inventor: Greg Eberl, Filing Date: Feb. 25, 2005 (11 pages).
Office Action dated Dec. 1, 2009 in U.S. Appl. No. 11/067,535; Inventor: Greg Eberl, Filing Date: Feb. 25, 2005 (12 pages).
Amendment dated Feb. 1, 2010 in U.S. Appl. No. 11/067,535; Inventor: Greg Eberl, Filing Date: Feb. 25, 2005 (12 pages).
Advisory Action dated Feb. 18, 2010 in U.S. Appl. No. 11/067,535; Inventor: Greg Eberl, Filing Date: Feb. 25, 2005 (3 pages).
Amendment dated Jun. 30, 2009 in U.S. Appl. No. 11/031,629; Inventor: David K. Swanson, Filing Date: Jan. 8, 2005 (12 pages).
Office Action dated Aug. 6, 2009 in U.S. Appl. No. 11/031,629; Inventor: David K. Swanson, Filing Date: Jan. 8, 2005 (7 pages).
Amendment dated Nov. 10, 2009 in U.S. Appl. No. 11/031,629; Inventor: David K. Swanson, Filing Date: Jan. 8, 2005 (11 pages).
Notice of Allowance dated Jan. 27, 2010 in U.S. Appl. No. 11/031,629; Inventor: David K. Swanson, Filing Date: Jan. 8, 2005 (4 pages).

* cited by examiner

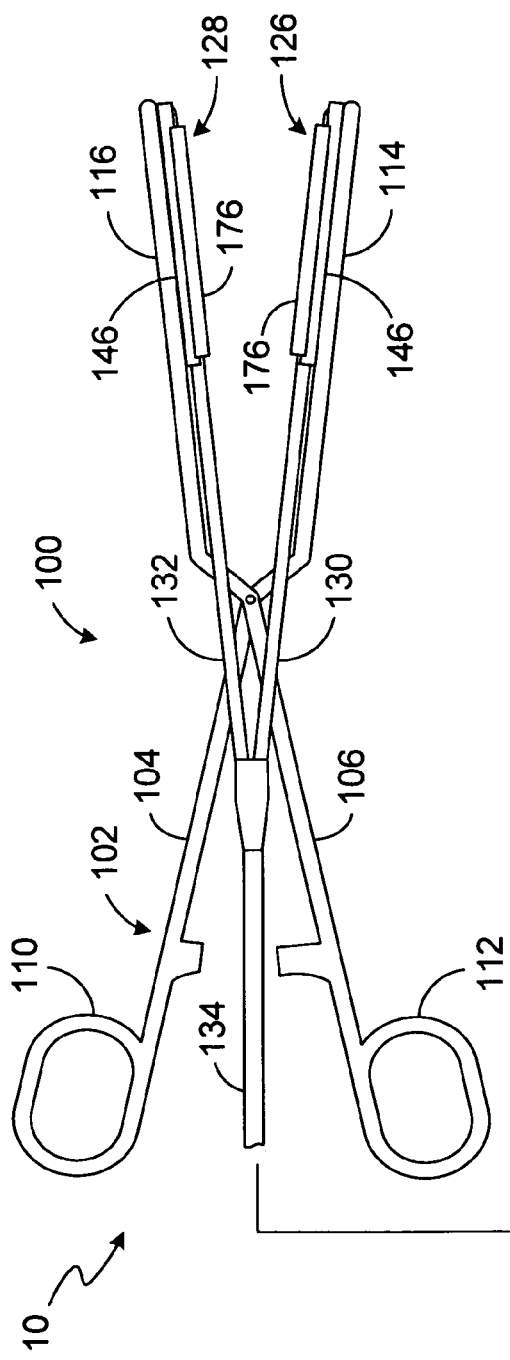
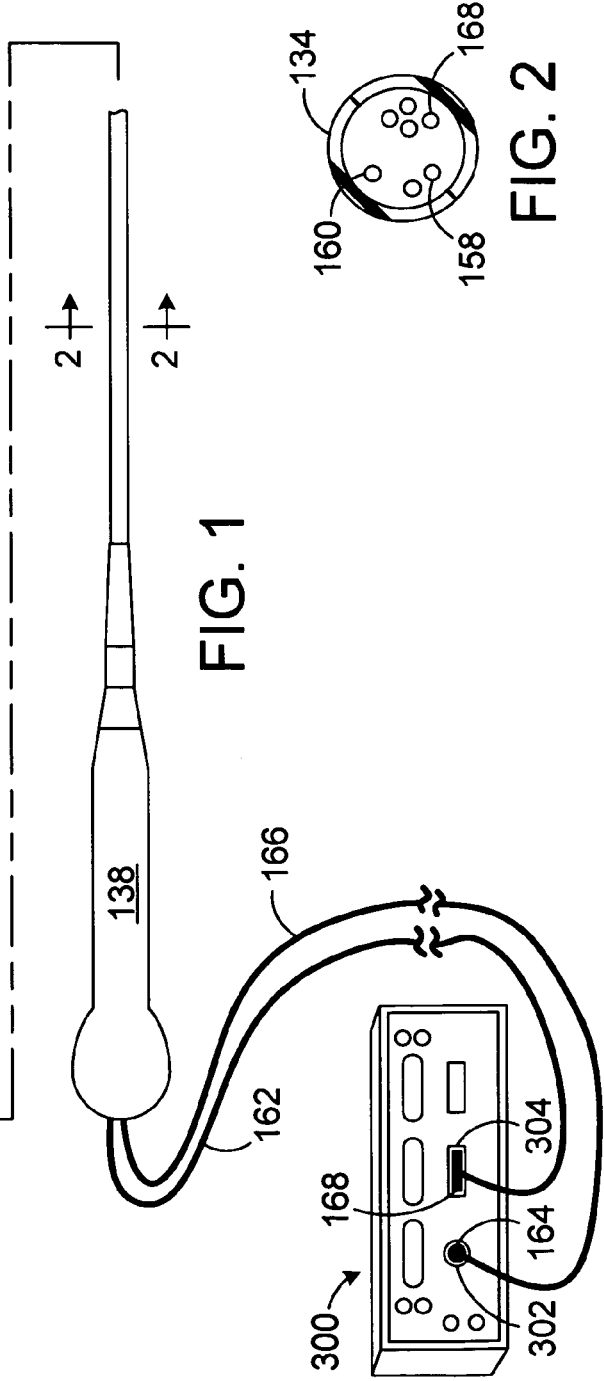
FIG. 1
FIG. 2

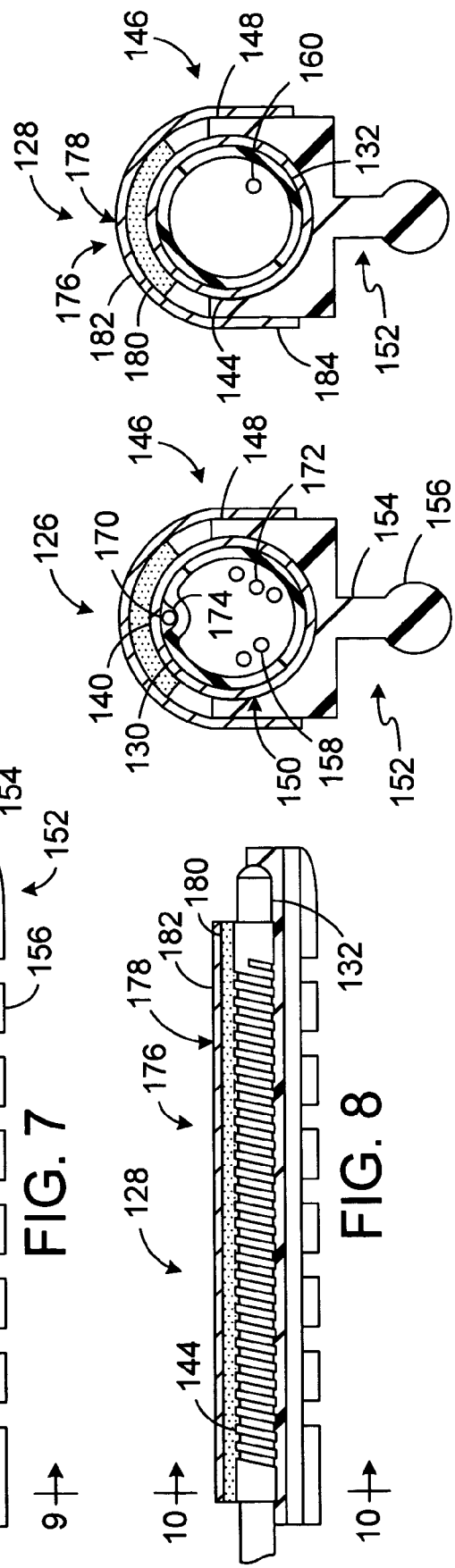
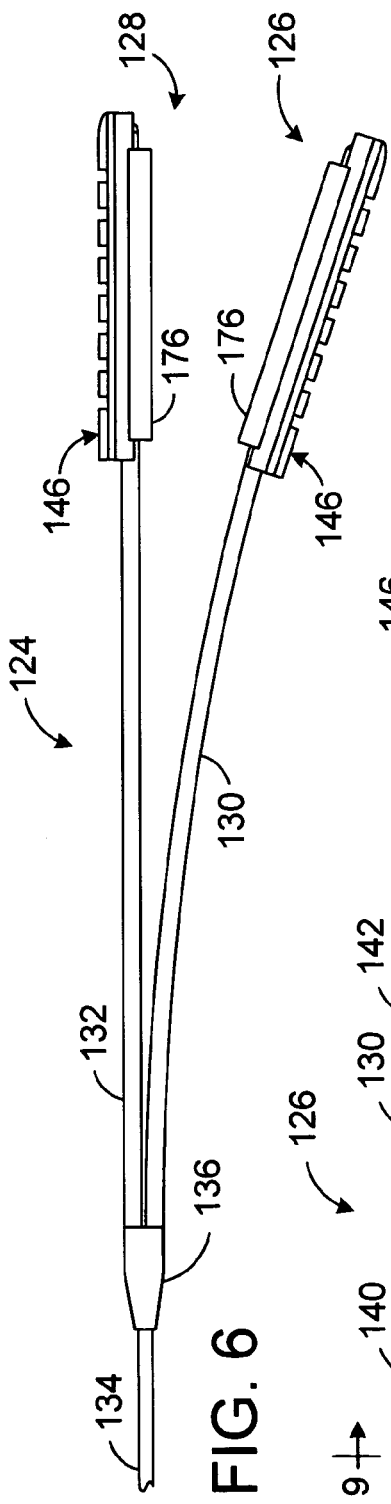
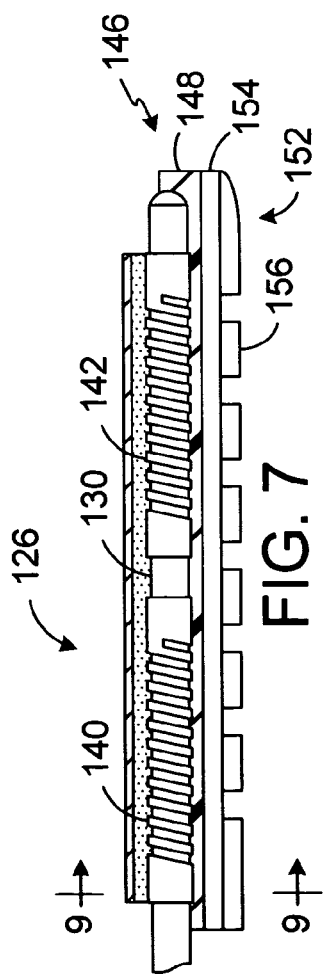

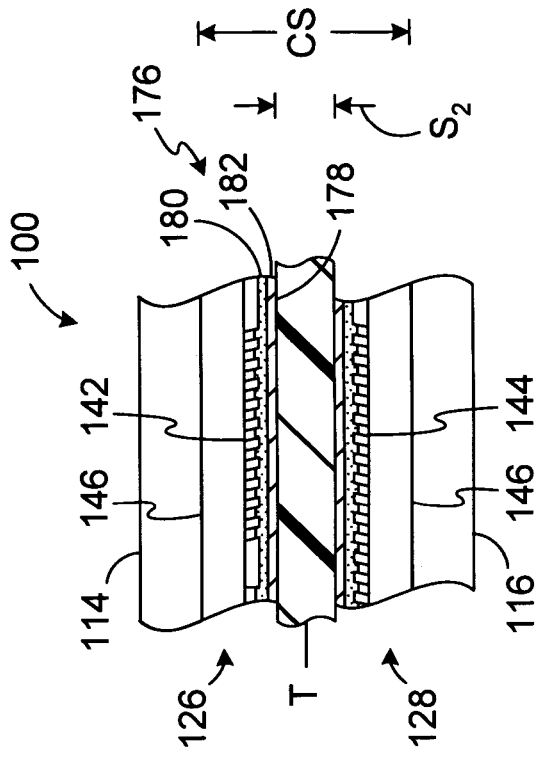
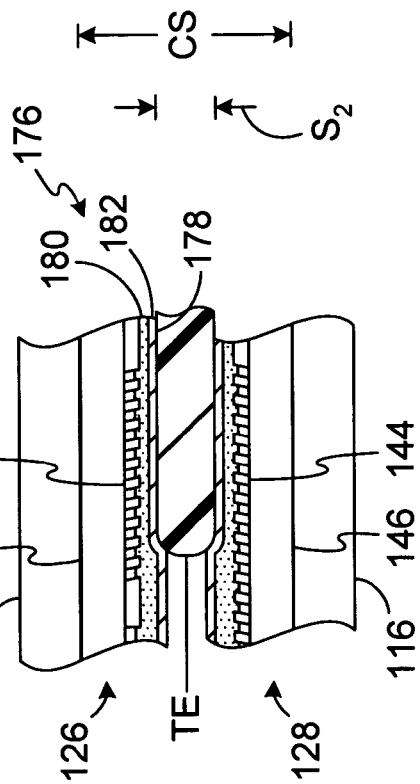
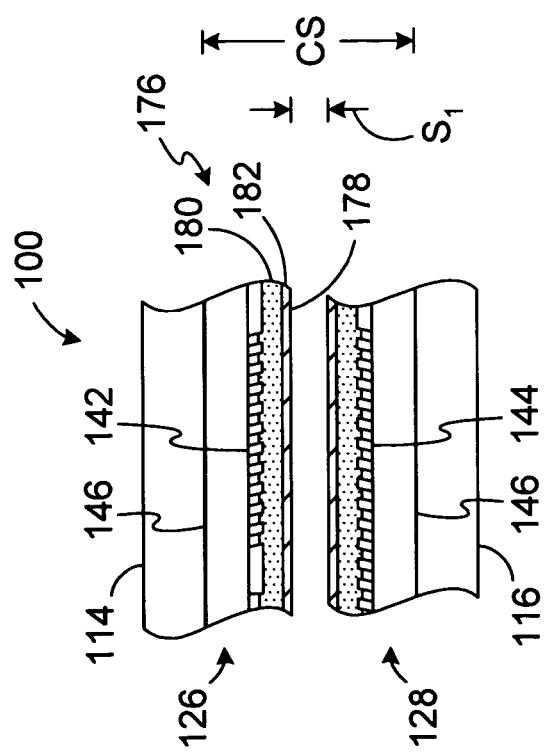

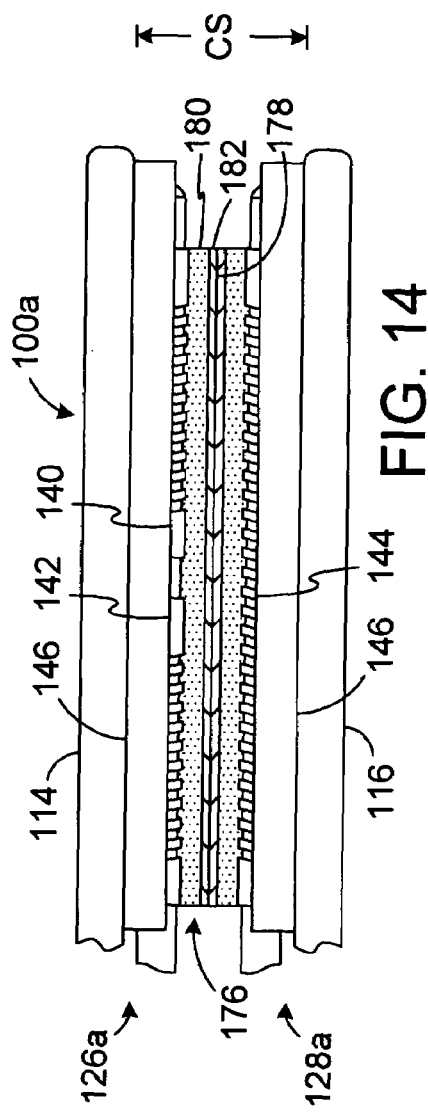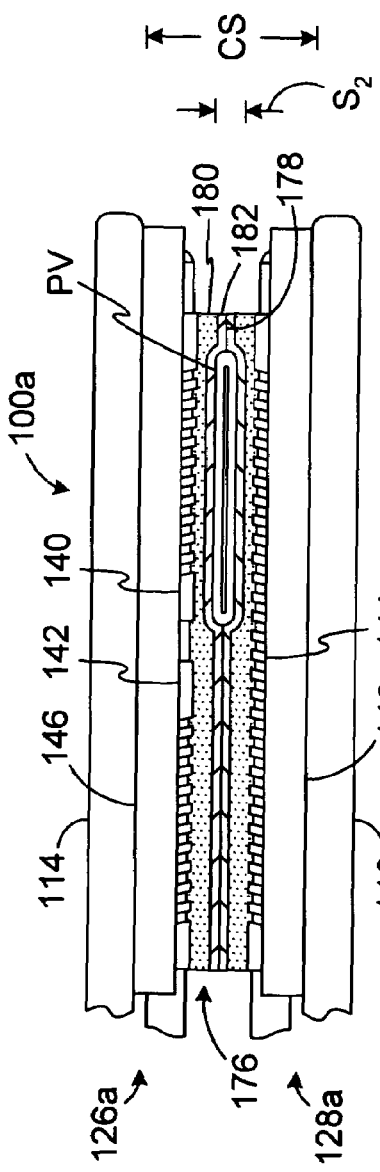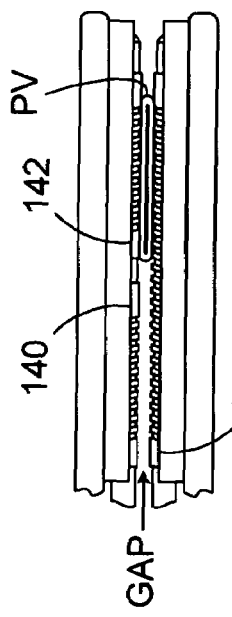

 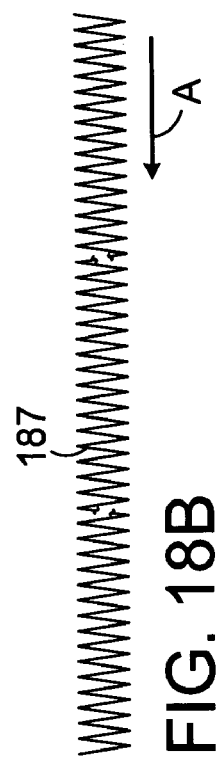 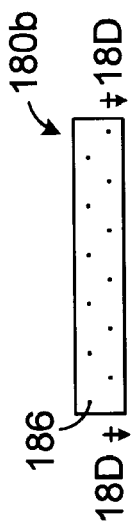 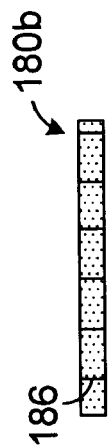 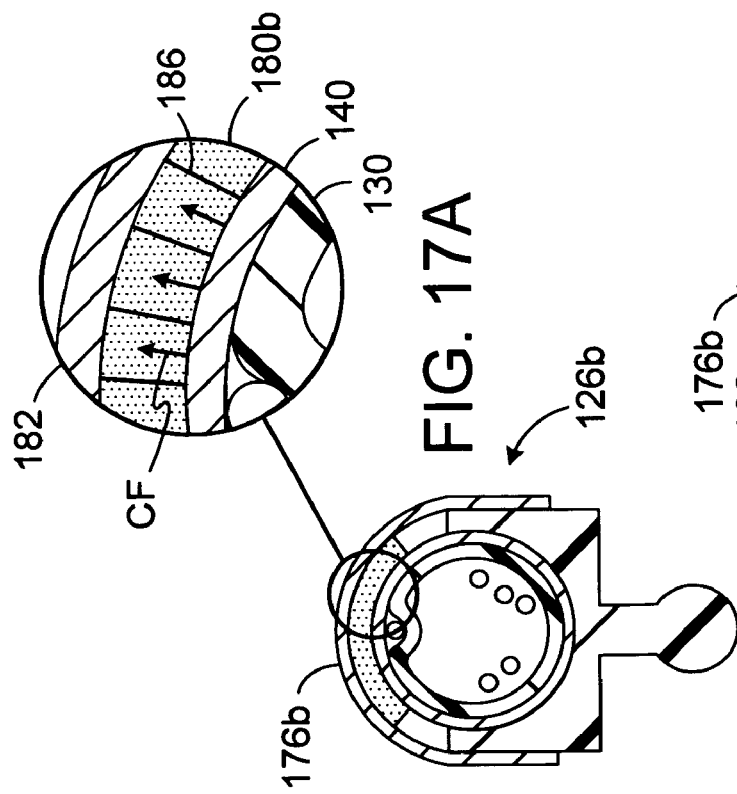 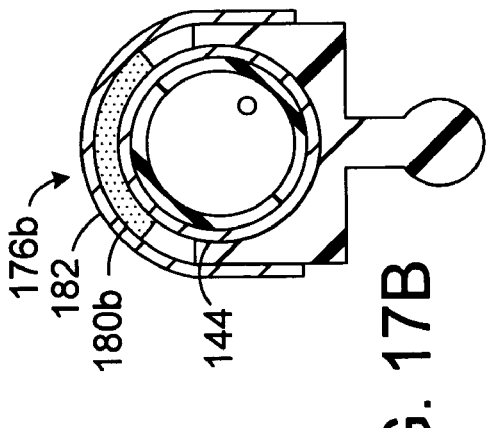

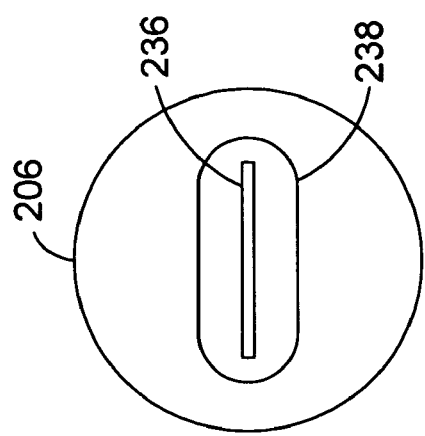
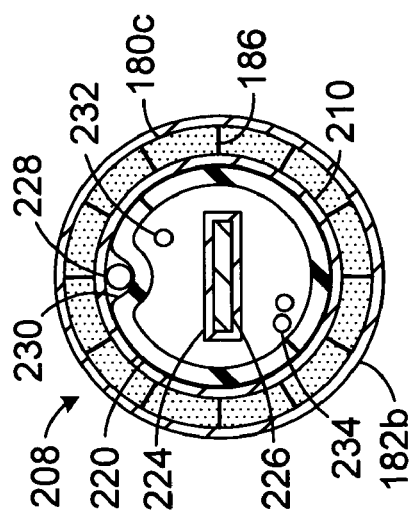
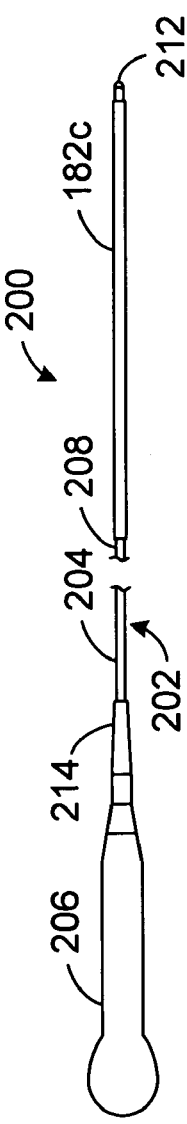
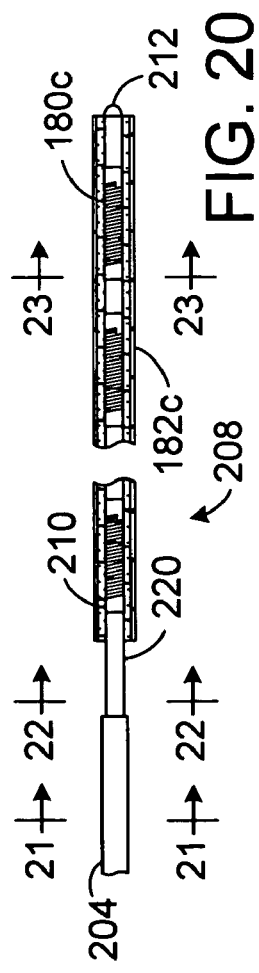
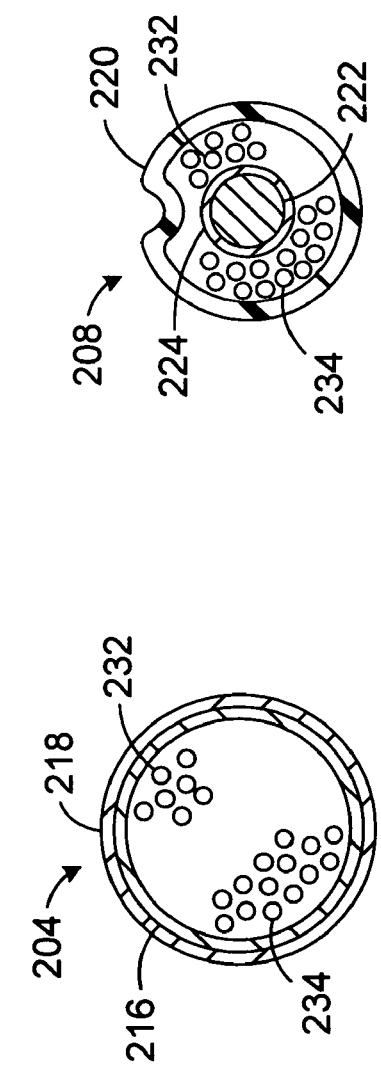

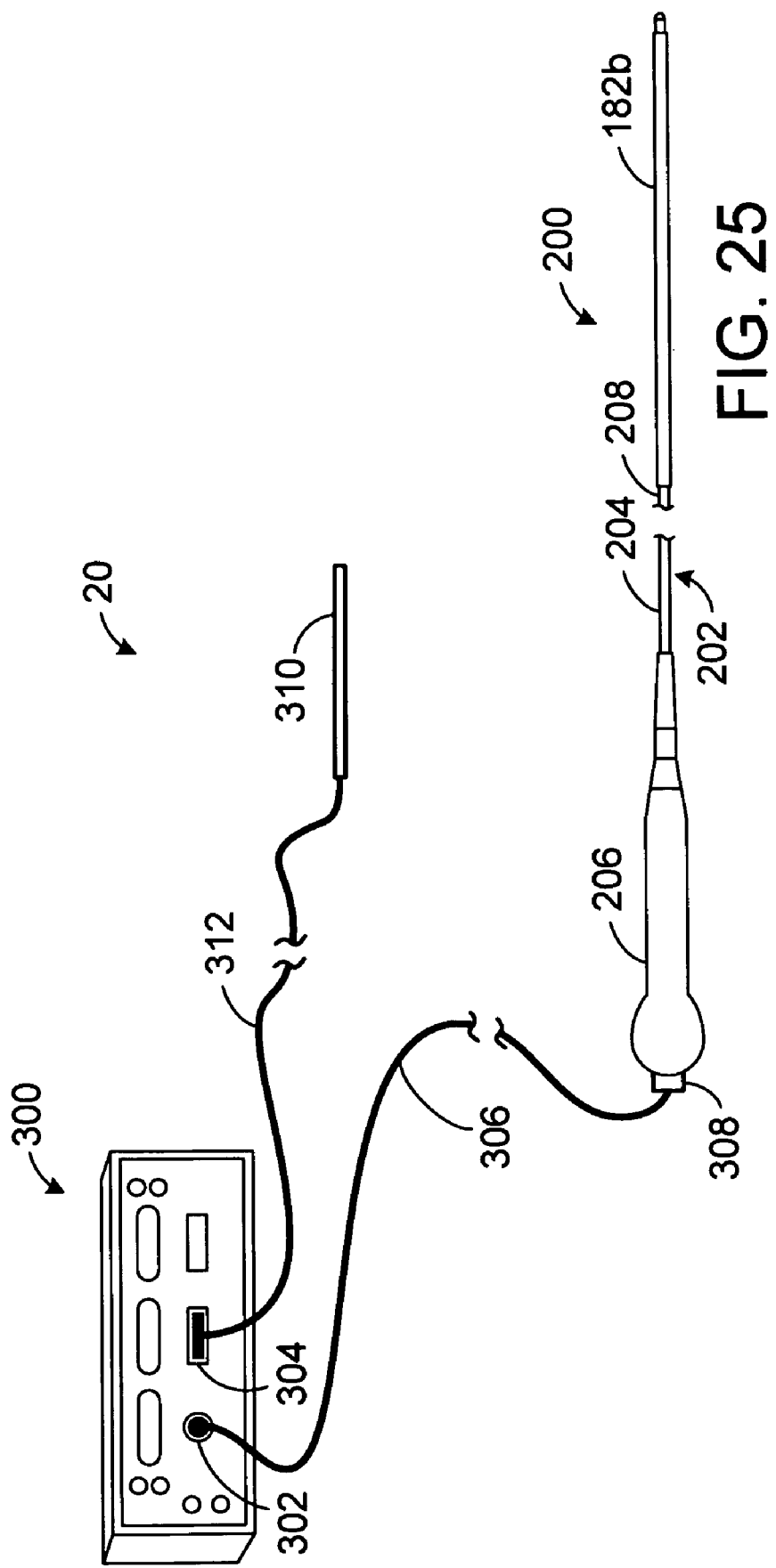

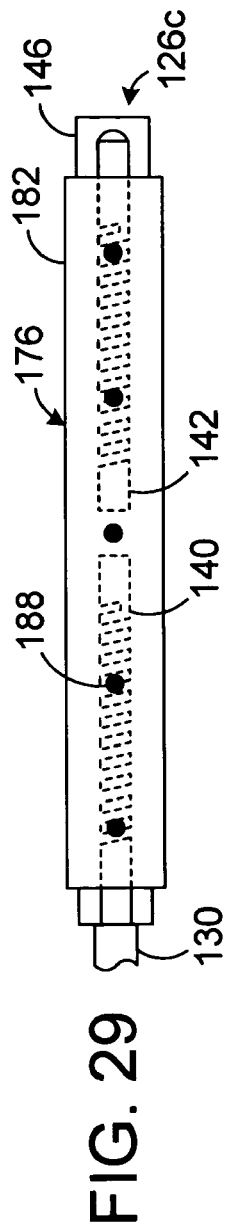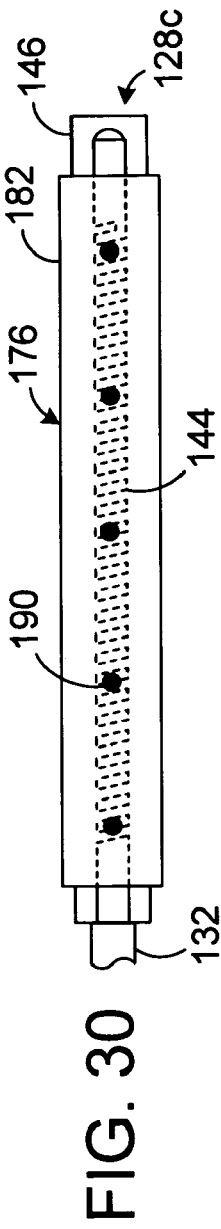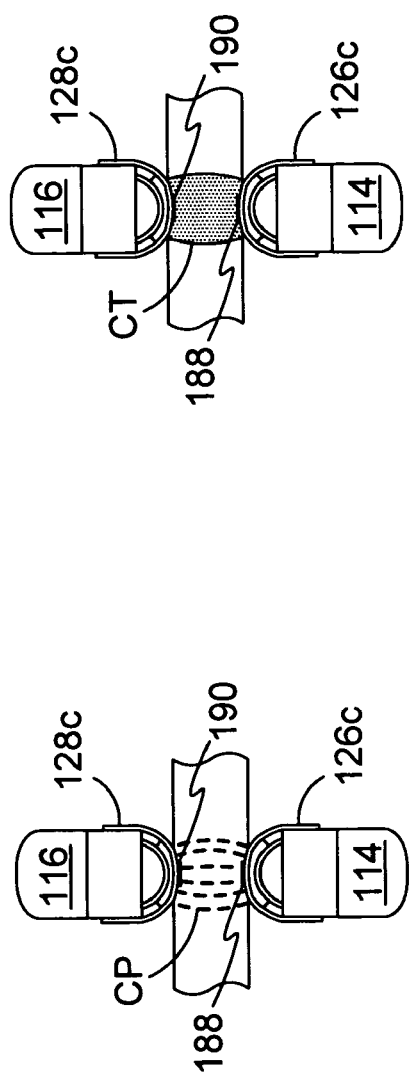

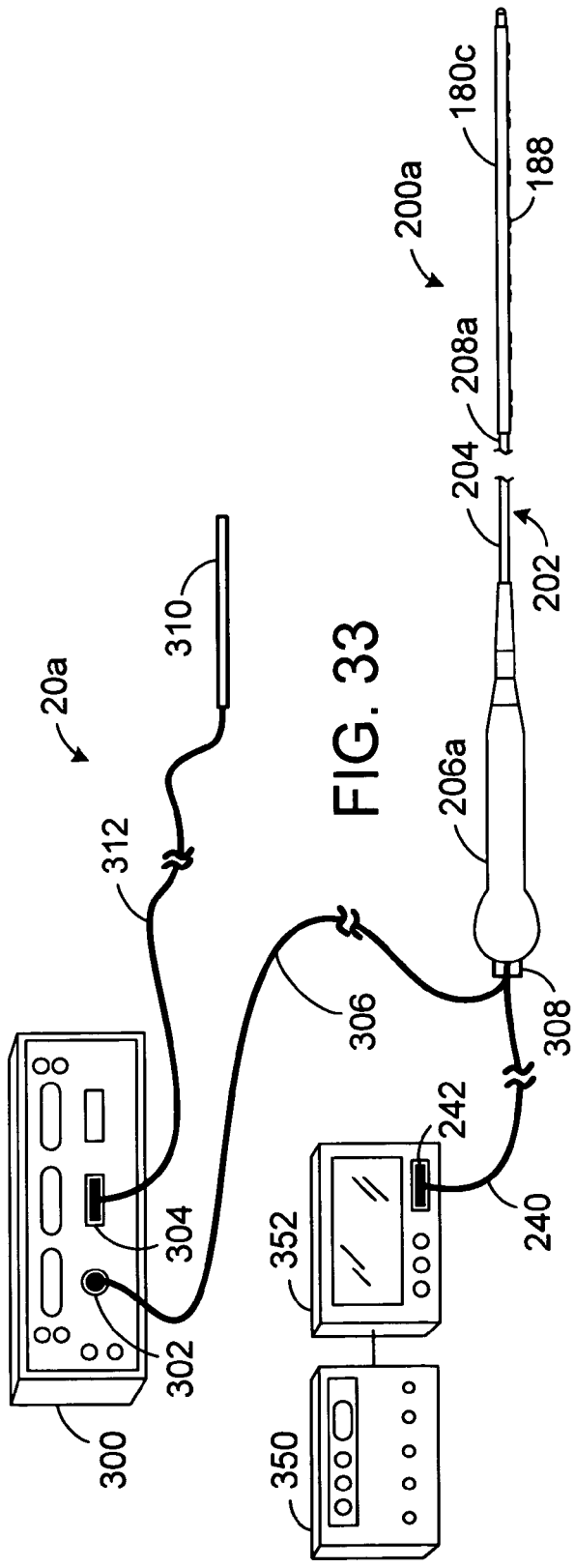
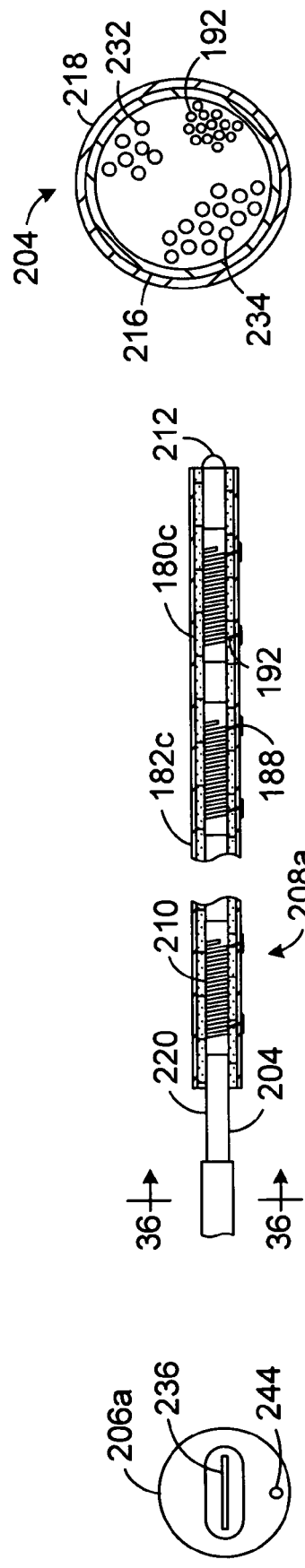

WETTABLE STRUCTURES INCLUDING CONDUCTIVE FIBERS AND APPARATUS INCLUDING THE SAME

BACKGROUND OF THE INVENTIONS

1. Field of Inventions

The present inventions relate generally to devices for performing therapeutic operations on body tissue.

2. Description of the Related Art

There are many instances where electrosurgical devices are used to form therapeutic lesions in tissue. Therapeutic lesions are frequently formed to treat conditions in the heart, prostate, liver, brain, gall bladder, uterus, breasts, lungs and other solid organs. Electromagnetic radio frequency ("RF") may, for example, be used to heat and eventually kill (i.e. "ablate") tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. The tissue coagulation energy is typically supplied and controlled by an electrosurgical unit ("ESU") during the therapeutic procedure. More specifically, after an electrosurgical device has been connected to the ESU, and the electrodes or other energy transmission elements on the device have been positioned adjacent to the target tissue, energy from the ESU is transmitted through the energy transmission elements to the tissue to from a lesion. The amount of power required to coagulate tissue ranges from 5 to 150 W.

Clamps that carry electrodes or other energy transmission elements on opposable clamp members are used in a wide variety of electrophysiology procedures, especially those in which the physician intends to position electrodes on opposite sides of a body structure. Examples of clamp based devices which carry energy transmission elements are disclosed in U.S. Pat. No. 6,142,994, and U.S. Patent Pub. No. 2003/0158547 A1, which are incorporated herein by reference. In a typical clamp based procedure, a clamp will be used by the physician to position energy transmission surfaces (such as the outer surface of the exposed portion of the energy transmission elements) on opposite sides of a tissue structure. Energy may then be transmitted through the tissue from one energy transmission surface to the other, which is commonly referred to as bipolar energy transmission, or from each of the energy transmission surfaces to an indifferent electrode positioned at a remote location such as the patient's skin, which is commonly referred to as unipolar energy transmission.

Surgical probes are another example of devices that may be used in electrophysiology procedures. Surgical probes used to create lesions often include a handle, a relatively short shaft that is from 4 inches to 18 inches in length and either rigid or relatively stiff, and a distal section that is from 1 inch to 10 inches in length and either malleable or somewhat flexible. One or more coagulation electrodes or other energy transmission devices are carried by the distal section. Surgical probes are used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994.

Tissue contact is an important issue in any electrophysiology procedure. With respect to clamp based procedures, for example, the failure to achieve and maintain intimate contact between the tissue and energy transmission surfaces can result in gaps in what were intended to be continuous linear or curvilinear lesions. With respect to the formation of therapeutic lesions in the heart to treat cardiac conditions such as atrial fibrillation, atrial flutter and arrhythmia, such gaps may result in a failure to cure the arrhythmia and atrial flutter or may create atrial flutter. Moreover, atrial flutter created by gaps in linear lesions can difficult to cure. Poor contact between the tissue and energy transmission surfaces can also result in lesions that are not transmural. Lesions which are not transmural may, in turn, fail to cure the patient's arrhythmia or other medical condition.

One method of insuring the proper level of contact in clamp based electrophysiology procedures is to configure the clamp in such a manner that there is a predetermined (i.e. preset) spacing between the energy transmission surfaces when the clamp is in the closed orientation that corresponds to the thickness of the target tissue structure. In addition to insuring intimate tissue contact, the preset spacing also prevents the mechanical damage to tissue (e.g. cutting through the tissue structure) that can occur when the spacing between the energy transmission surfaces is less than the thickness of the target tissue structure when the clamp is closed. For example, electrophysiology clamps that are intended to position energy transmission surfaces on opposite sides of the tissue around the pulmonary veins have a closed orientation spacing of about 2 mm between the energy transmission surfaces.

The present inventors have determined that conventional clamp based electrophysiology devices are susceptible to improvement. More specifically, the present inventors have determined that there are procedures where a physician may wish to form lesions in tissue structures with different thicknesses. The use of a conventional clamp based electrophysiology device with a preset spacing between the energy transmission surfaces can hamper such procedures because a preset spacing that is large enough to accommodate the larger tissue structures may be too large to facilitate intimate tissue contact with the smaller tissue structures. As such, the use of a single conventional clamp based electrophysiology device in procedures that involve tissue structures of varying thickness may result in mechanical damage to tissue and/or lesions that are not continuous or transmural.

Another important issue in electrophysiology procedures is energy transmission and, more specifically, the electrical resistivity on the structure that is in contact with tissue. In some clamp and surgical probe based electrophysiology devices that include electrodes, the exposed portions of the electrodes are covered with porous, wettable structures that are configured to be saturated with and retain ionic fluid (such as saline) prior to use. Tissue coagulation energy may be transmitted to (or to and from) the electrodes by way of the ionic fluid. The present inventors have determined that conventional porous, wettable structures are susceptible to improvement and, in particular, that the electrical resistance across the porous, wettable structures should be reduced.

Still another important issue in electrophysiology procedures is confirming whether a therapeutic lesion has been properly formed during surgical procedures. Some clamp and surgical probe based electrophysiology devices employ stimulation electrodes that may be placed on tissue on one side of a lesion, or stimulation and sensing electrodes that may be placed on tissue on opposite sides of a lesion, and used to confirm whether a therapeutic lesion has been formed during surgical procedures. The present inventors have determined that such clamp and surgical probe based electrophysiology devices are susceptible to improvement.

SUMMARY OF SOME OF THE INVENTIONS

An apparatus for use with a clamp in accordance with one invention herein includes first and second energy transmission surfaces with a predetermined spacing when the clamp is closed and a device that allows the spacing to increase when the energy transmission surfaces are brought into contact with a tissue structure that is thicker than the predetermined spacing. Similarly, a clamp in accordance with one invention herein includes first and second energy transmission surfaces with a predetermined spacing when the clamp is closed and a device that allows the spacing to increase when the energy transmission surfaces are brought into contact with a tissue structure that is thicker than the predetermined spacing. Such devices provide a number of advantages. For example, such devices may be used to achieve and maintain intimate contact between the tissue and energy transmission surfaces, but will not damage tissue, when brought into contact with the tissue surfaces structures of varying thickness.

An apparatus for use with an energy transmission element in accordance with one invention herein includes a wettable structure configured to be saturated with and retain ionic fluid and a plurality of conductive fibers carried by the wettable structure. Such an apparatus provides a number of advantages. For example, the use of conductive fibers greatly increases the conductivity of the apparatus, as compared to an otherwise identical wettable structure saturated with the same ionic fluid.

An apparatus in accordance with one invention herein includes a tissue coagulation device that creates a current path and a stimulation electrode carried within the current path. Such an apparatus provides a number of advantages. For example, the apparatus allows the physician to quickly and easily confirm tissue contact, form a lesion, and evaluate the lesion with the same apparatus and without moving the apparatus. The location of the stimulation electrode also results in more accurate information concerning the lesion, as compared to conventional apparatus, because the assessment of the lesion is localized (i.e. the assessment is made directly on the target tissue within the current path).

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a perspective view of a surgical system in accordance with one embodiment of a present invention.

FIG. 2 is a section view taken along line 2-2 in FIG. 1.

FIG. 6 is a plan view of a portion of a tissue coagulation assembly in accordance with one embodiment of a present invention.

FIG. 7 is a side, partial section view of a portion of the tissue coagulation assembly illustrated in FIG. 6.

FIG. 8 is a side, partial section view of a portion of the tissue coagulation assembly illustrated in FIG. 6.

FIG. 9 is a section view taken along line 9-9 in FIG. 7.

FIG. 10 is a section view taken along line 10-10 in FIG. 8.

FIG. 11 is a side, partial section view of a portion of the electrophysiology clamp apparatus illustrated in FIG. 1 in the closed orientation.

FIG. 12 is a side, partial section view of a portion of the electrophysiology clamp apparatus illustrated in FIG. 1 in the closed orientation engaging a tissue structure.

FIG. 13 is a side, partial section view of a portion of the electrophysiology clamp apparatus illustrated in FIG. 1 in the closed orientation engaging a tissue structure.

FIG. 14 is a side, partial section view of a portion of the electrophysiology clamp apparatus in accordance with one embodiment of a present invention in the closed orientation.

FIG. 15 is a side, partial section view of the portion of the electrophysiology clamp apparatus illustrated in FIG. 14 engaging a tissue structure.

FIG. 16 is a side view of a portion of a modified version of the electrophysiology clamp apparatus illustrated in FIGS. 14 and 15.

FIG. 17A is a section view of an energy transmission device in accordance with one embodiment of a present invention.

FIG. 17B is a section view of an energy transmission device in accordance with one embodiment of a present invention.

FIG. 18A is a side view illustrating a step in a process in accordance with one embodiment of a present invention.

FIG. 18B is a top view illustrating a step in a process in accordance with one embodiment of a present invention.

FIG. 18C is a top view of a wettable structures with conductive fibers in accordance with one embodiment of a present invention.

FIG. 18D is a section view taken along line 18D-18D in FIG. 18C.

FIG. 19 is a plan view of a surgical probe in accordance with one embodiment of a present invention.

FIG. 20 is plan, partial section view of the distal portion of the surgical probe illustrated in FIG. 19.

FIG. 21 is a section view taken along line 21-21 in FIG. 20.

FIG. 22 is a section view taken along line 22-22 in FIG. 20.

FIG. 23 is a section view taken along line 23-23 in FIG. 20.

FIG. 24 is an end view of the surgical probe illustrated in FIG. 19.

FIG. 25 is a perspective view of a surgical system in accordance with one embodiment of a present invention.

FIG. 29 is a plan view of a portion of the tissue coagulation assembly illustrated in FIG. 26.

FIG. 30 is a plan view of a portion of the tissue coagulation assembly illustrated in FIG. 26.

FIGS. 31 and 32 are end views showing portions of a lesion formation process in accordance with one embodiment of a present invention.

FIG. 33 is a perspective view of a surgical system in accordance with one embodiment of a present invention.

FIG. 34 is an end view of the surgical probe illustrated in FIG. 33.

FIG. 35 is a side, partial section view of a portion of the surgical probe illustrated in FIG. 33.

FIG. 36 is a section view taken along line 36-36 in FIG. 35.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Exemplary Surgical Systems
III. Exemplary Wettable Structures With Conductive Fibers
IV. Power Control
V. Stimulation Electrodes and Lesion Confirmation The section titles and overall organization of the present detailed description are for the purpose of convenience only and are not intended to limit the present inventions.

I. Introduction

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus, breasts, lungs, and other solid organs.

II. Exemplary Surgical Systems

As illustrated for example in FIG. 1, an exemplary surgical system 10 in accordance with one embodiment of a present invention includes an electrophysiology clamp apparatus 100 and an ESU 300. The ESU 300, which is discussed in Section IV below, supplies and controls power to the electrophysiology clamp apparatus 100. The electrophysiology clamp apparatus 100 includes a clamp and a tissue coagulation assembly that may be secured to the clamp. As used herein, the term "clamp" includes, but is not limited to, clamps, clips, forceps, hemostats, and any other surgical device that includes a pair of opposable clamp members that hold tissue, at least one of which is movable relative to the other. In some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

Figure 4:
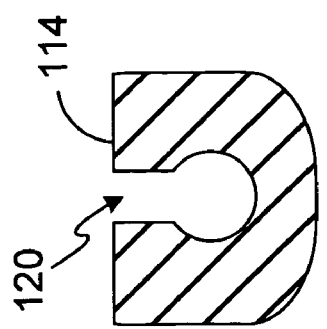
FIG. 4 is a section view taken along line 4-4 in FIG. 3.
Figure 3:
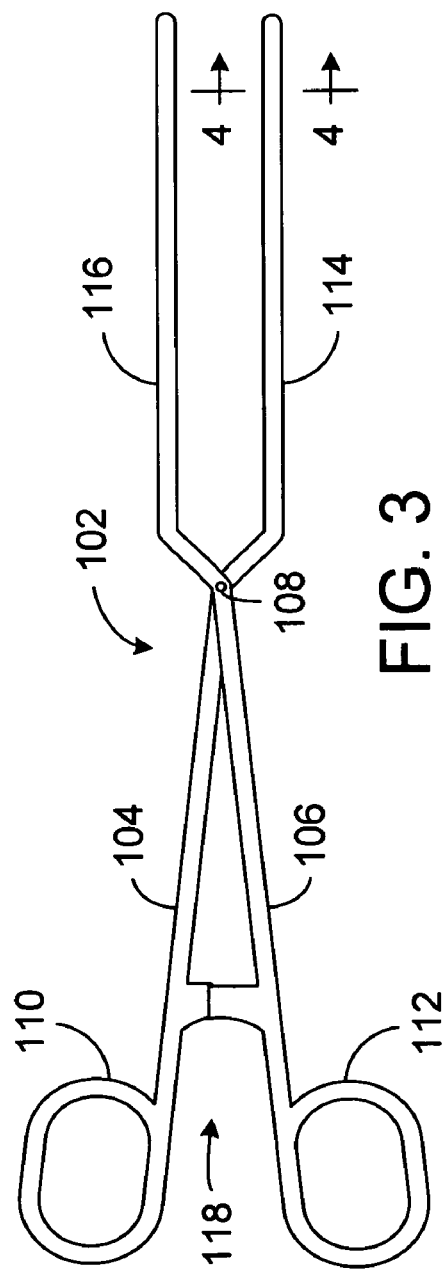
FIG. 3 is a plan view of a clamp in accordance with a preferred embodiment of a present invention.
Figure 5:
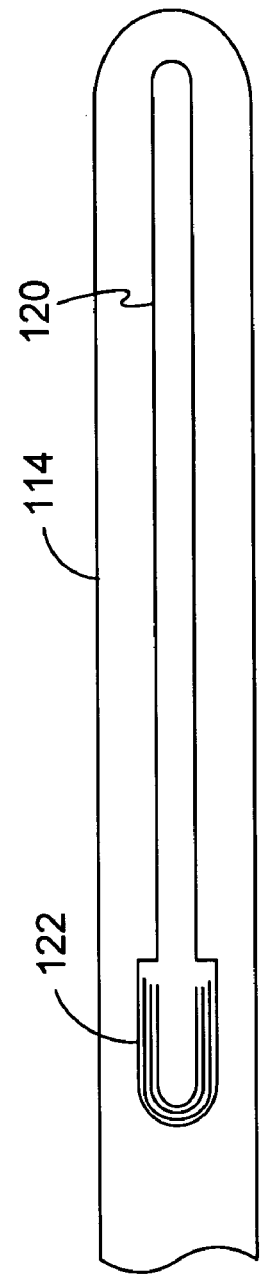
FIG. 5 is a top view of a portion of the clamp illustrated in FIG. 3.

One example of a clamp is generally represented by reference numeral 102 in FIGS. 1 and 3-5. Referring more specifically to FIGS. 3-5, the clamp 102 includes a pair of rigid arms 104 and 106 that are pivotably connected to one another by a pin 108. The proximal ends of the arms 104 and 106 are respectively connected to a pair handle members 110 and 112, while the distal ends are respectively connected to a pair of clamp members 114 and 116. The clamp members 114 and 116 may be rigid or malleable and, if rigid, may be linear or have a pre-shaped curvature. A locking device 118 locks the clamp in the closed orientation, and prevents the clamp members 114 and 116 from coming any closer to one another than is illustrated in FIGS. 3 and 11-13, thereby defining a predetermined (or preset) spacing between the clamp members. The clamp 102 is also configured for use with a pair of soft, deformable inserts (not shown) that may be removably carried by the clamp members 114 and 116 and allow the clamp to firmly grip a bodily structure without damaging the structure. To that end, the clamp members 114 and 116 each include a slot 120 (FIGS. 4 and 5) that is provided with a sloped inlet area 122 and the inserts include mating structures that are removably friction fit within the slots. The present tissue coagulation and stimulation assemblies may be mounted on the clamp members in place of the inserts.

With respect to the tissue coagulation assembly, the tissue coagulation assembly 124 in the exemplary electrophysiology clamp apparatus 100 illustrated in FIG. 1 includes a first energy transmission device 126 that may be connected to one of the clamp members 114 and 116 and a second energy transmission device 128 that may be connected to the other. The energy transmission devices 126 and 128 are respectively carried on support structures 130 and 132, which are connected to a cable 134 by a molded junction 136. The other end of the cable 134 enters a handle 138. The support structures 130 and 132 in the illustrated embodiment are flexible tubular structures which have an outer diameter that is, depending on the diameter of the electrodes 140, 142 and 144 (discussed below), typically between about 1.5 mm and about 3 mm. The support structures 130 and 132 in the illustrated embodiment, which are intended for use in cardiovascular applications, have an outer diameter of about 2 mm. Suitable support structure materials include, for example, flexible biocompatible thermoplastic tubing such as unbraided Pebax® material, polyethylene, or polyurethane tubing.

Although tissue coagulation assemblies in accordance with the present inventions may be operated in bipolar and unipolar modes, the exemplary tissue coagulation assembly 124 is configured so as to be especially useful in a bipolar mode wherein the first energy transmission device 126 will transmit energy through tissue to the second energy transmission device 128. To that end, and as illustrated for example in FIGS. 7 and 8, the first energy transmission device 126 includes a pair of electrodes 140 and 142 that may be independently controlled, while the second energy transmission device 128 includes a single electrode 144. Such an arrangement provides for higher fidelity control of the overall region that is transmitting energy and a gap free, constant potential region on the return side.

The spaced electrodes 140, 142 and 144 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil electrodes are disclosed in U.S. Pat. Nos. 5,797,905 and 6,245,068.

Alternatively, the electrodes 140, 142 and 144 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed. Still other types of electrodes are formed from electroless plated copper on a polyimide film or tubular substrate. Gold, nickel or silver should be plated over the copper for electrochemical stability and improved biocompatibility. The plating can be applied in continuous form (up to about 1-2 cm in length at most) or can be applied in a pattern that is designed to improve current density distributions and/or electrode flexing characteristics. Temperature sensors (e.g. thermocouples) may be incorporated into the electrode structure by placing the temperature sensors in a channel in the polyimide film or tubular substrate and then plating over them.

The electrodes 140 and 142 are preferably about 1.5 cm to 4 cm in length with about 1 mm to 3 mm spacing, which will result in the creation of continuous lesion patterns in tissue when coagulation energy is applied simultaneously to adjacent electrodes. The length of the electrode 144 is preferably the combined length of the electrodes 140 and 142, including the spacing therebetween, so that the overall electrode length on the first and second energy transmission devices 126 and 128 is the same.

The first and second energy transmission devices 126 and 128 in the embodiment illustrated in FIGS. 1 and 6-13 are also provided with respective mounting devices 146 that may be used to mount the tissue coagulation assembly 124 in general, and the energy transmission devices in particular, on the clamp 102. Additionally, although the configuration of the tissue coagulation assembly 124 may vary from application to application to suit particular situations, the exemplary tissue coagulation assembly is configured such that the electrodes 140 and 142 will be parallel to the electrode 144 when the clamp 102 is in the closed orientation.

Referring more specifically to FIGS. 7-10, the mounting devices 146 are identical in the illustrated embodiment. Each mounting device 146 includes a base member 148 that has a groove 150 which is configured to receive the support structure 130 and electrodes 140 and 142 (or support structure 132 and electrode 144). About 20% of the electrode surface (i.e. about 75° of the 360° circumference) is exposed in the illustrated embodiment. Adhesive may be used to hold the support structures and electrodes in place. The mounting device also includes a connector 152 that is configured to removably mate with the clamp slot 120 (FIGS. 4 and 5). The exemplary connector 152 is provided with a relatively thin portion 154 and a relatively wide portion 156, which may consist of a plurality of spaced members (as shown) or an elongate unitary structure, in order to correspond to the shape of the slot 120.

The mounting devices 146 are preferably formed from polyurethane. The length of the mounting devices 146 will vary according to the intended application. In the area of cardiovascular treatments, it is anticipated that suitable lengths will range from, but are not limited to, about 4 cm to about 10 cm. In the exemplary implementation, the mounting devices 146 are about 7 cm in length.

The electrodes 140 and 142 in the exemplary tissue coagulation assembly 124 are connected to power wires 158, while the electrode 144 is connected to a power wire 160, as shown in FIGS. 9 and 10. The power wires 158 and 160 extend through the support structures 130 and 132, respectively, as well as the cable 134, and into the handle 138. The power wires 158 extend into a cable 162 (FIG. 1) with a power connector 164 that extends proximally from the handle 136, while the power wire 160 extends into a cable 166 with a return connector 168 that also extends proximally from the handle.

A plurality of temperature sensors 170 (FIG. 9), such as thermocouples or thermistors, may be located on, under, abutting the longitudinal end edges of, or in between, the electrodes 140 and 142. A reference thermocouple (not shown) may also be provided. In the exemplary implementation, temperature sensors 170 are located at both longitudinal ends of each of the electrodes 140 and 142. The temperature sensors 170 are connected to signal wires 172, which pass through the support structure 130, cable 134 and cable 162. The temperature sensors 170 are also located within a linear channel 174 that is formed in the support structure 130. The linear channel insures that the temperature sensors will all face in the same direction (e.g. facing tissue) and be arranged in linear fashion.

The energy transmission devices 126 and 128 also include variable spacing structures 176, as is shown in FIGS. 1 and 6-13. The variable spacing structures 176, which are substantially identical in the illustrated embodiment and each define an energy transmission surface 178, allow the energy transmission devices 126 and 128 to achieve intimate tissue contact with tissue structures of varying thickness without mechanically damaging the thicker structures. Referring more specifically to FIGS. 11 and 12, the exemplary clamp apparatus 100 is configured such that there is a preset spacing CS between the clamp members 114 and 116 when the clamp 102 is in the completely closed orientation. The energy transmission devices 126 and 128 and variable spacing structures 176 are correspondingly configured such that there is a preset spacing $S_1$ between the energy transmission surfaces 178 when the clamp 102 is in the closed orientation illustrated in FIG. 11. When the clamp apparatus 100 is closed on opposite sides of a tissue structure T that is thicker than the spacing $S_1$, the variable spacing structures 176 will compress, and the spacing between the energy transmission surfaces 178 will increase to $S_2$ as shown in FIG. 12, in order to accommodate the tissue structure. The spacing CS between the clamp members 114 and 116 will, however, remain the same. The variable spacing structures 176 are preferably configured such that as they compress from the state illustrated in FIG. 11 to the state illustrated in FIG. 12, there will not be a significant increase in the clamping force applied to a tissue structure therebetween.

Another advantage associated with the variable spacing structures 176 is associated with tissue contact at the edge of a tissue structure. As illustrated in FIG. 13, the resiliency of the variable spacing structures 176 allows the energy transmission surfaces 178 to wrap around the tissue structure edge TE, thereby providing better contact along the edge than could be achieved with a more rigid energy transmitting structure that would not wrap around the edge. Better contact results in better lesions and reduces the likelihood that there will be gaps in a lesion at the edge of a tissue structure.

In implementations intended for use in the treatment of cardiac conditions such as atrial fibrillation, for example, the spacing $S_1$ between the energy transmission surfaces 178 may be about 1 mm and the spacing $S_2$ may be about 2 mm. As such, the energy transmission devices 126 and 128 will achieve and maintain intimate contact between the tissue and energy transmission surfaces 178 when brought into contact with the epicardial and endocardial surfaces that are about 1 mm apart (typically by inserting one of the energy transmission through a cut in the left atrial wall), but will not damage tissue when positioned on opposite sides of the tissue around the pulmonary veins, which is about 2 mm thick after the opposite sides are brought together.

Although the present inventions are not limited to any particular instrumentality for facilitating the increase in spacing when a target tissue structure is thicker than the preset spacing $S_1$, the exemplary variable spacing structures 176 include a resilient member 180 and a barrier member 182. Referring to FIGS. 11-13, the resilient members 180 in the exemplary implementation are configured to compress in the manner described above, thereby acting as cushions for tissue structures that are thicker than the preset spacing $S_1$. The resilient members 180 are also porous, wettable structures that are configured to be saturated with and retain ionic fluid (such as saline) prior to use so that energy may be transmitted to and from the associated electrodes by way of the ionic fluid. Suitable materials include foams, such as open cell foams, reticulated foams, non-reticulated foams, fine cell foams and hydrocolloide foams. Other suitable materials include hydrogels, thick woven biocompatible materials (e.g. Dacron®), cotton and cellulose. The thickness of the resilient members 180 (i.e. the distance from the outer surface of the associated electrode to the inner surface of the associated barrier member) may range from about 1 mm to 3 mm and is about 1.5 mm in the illustrated embodiment.

Turning to the barrier members 182 in the exemplary variable spacing structures 176, each barrier member is preferably a porous structure that is used to secure the associated resilient member 180 in place. To that end, the side edges 184 of the barrier members 182 are secured to the mounting device base members 148 (FIG. 10). The barrier members 182, the outer surfaces of which define the energy transmission surfaces 178, are also preferably porous and are hydrophilic so that they may retain the aforementioned ionic fluid through which energy is transmitted during electrophysiology procedures. The thickness of the barrier members 182 may range from about 0.05 mm to 0.5 mm and is about 0.2 mm in the illustrated embodiment.

The barrier members 182 may also be used to perform a number of other functions. For example, the barrier members 182 prevent tissue ingress into the resilient member 180 during electrophysiology procedures, which can result in the tissue sticking to the resilient member and tissue tearing when the energy transmission devices 126 and 128 are moved. Suitable materials for the barrier member 182 include biocompatible fabrics commonly used for vascular patches (such as woven Dacron®). One specific example is Hemashield Finesse™ from Boston Scientific Corporation. Such material may be easily cleaned during an electrophysiology procedure with alcohol or saline, which further facilitates the formation of multiple lesions with the same tissue coagulation assembly 124 during a single electrophysiology procedure.

It should be noted that the effective electrical resistivity of each variable spacing structure 176 when wetted with 0.9% saline (normal saline) should range from about 1 Ω-cm to about 2000 Ω-cm. A preferred resistivity for epicardial and endocardial procedures is about 1000 Ω-cm, which is much closer to the resistivity of tissue than that of the electrodes. As a result, energy transmission devices with the variable spacing structure 176 will have lower edge currents and provide more uniform current distribution than energy transmission device that are configured to place the electrodes in direct contact with tissue.

The distal portion of another exemplary clamp apparatus 100a is illustrated in FIGS. 14 and 15. The clamp apparatus 100a is essentially identical to the clamp apparatus 100 and similar elements are represented by similar reference numerals. The clamp apparatus 100a is, however, configured such that there is no spacing $S_1$ between the energy transmission surfaces 178, i.e. the energy transmission surfaces are in contact with one another, when the clamp 102 is in the closed orientation illustrated in FIG. 14. This may be accomplished by slightly modifying the dimensions of the clamp and/or the energy transmission devices. In the illustrated embodiments, the energy transmission devices 126a and 128a are slightly thicker than the energy transmission devices 126 and 128 in the clamp apparatus 100.

When the clamp apparatus 100a is closed on opposite sides of a tissue structure, such as the compressed pulmonary vein PV illustrated in FIG. 15, the associated portions of the variable spacing structures 176 will compress, and the spacing between the energy transmission surfaces 178 increase to $S_2$ in order to accommodate the tissue structure. The portions of the energy transmission surfaces 178 of the clamp apparatus 100a that are not in contact with a tissue structure will remain in contact with one another when other portions are in contact with a tissue structure. As a result, there will not be any electrically non-conductive gaps between the energy transmission surfaces 178.

The configuration illustrated in FIGS. 14 and 15 is advantageous for a number of reasons. For example, the entire surface of the tissue structure (e.g. the compressed pulmonary vein PV illustrated in FIG. 15), including the lateral edge surfaces, is in contact with a portion an energy transmission surface 178 of a variable spacing structure 176. As noted above, increasing the amount of edge tissue contacted by the energy transmission surfaces reduces the likelihood that there will be gaps in a lesion at the edge of the tissue structure.

Another advantage is associated with the portions of the energy transmission surfaces 178, and the underlying electrodes, that are not in contact with tissue. As discussed in Section IV below, power to the transmitting electrodes 140 and 142 may be controlled by the ESU 300 (FIG. 1) on an electrode-by-electrode basis. In some instances, the tissue coagulation procedure will be shut down when there is no current path from one of the transmitting electrodes 140 and 142 to the return electrode 144. In the exemplary implementation illustrated in FIGS. 14 and 15, such current paths are insured because the energy transmission surfaces 178 are either in contact with tissue or are in contact with one another.

Conversely, as illustrated in FIG. 16, when an otherwise identical electrophysiology clamp that lacks the variable spacing structures 176 is positioned around a pulmonary vein PV or other tissue structure, it is possible that there will be a gap between one of the transmitting electrodes 140 and 142 and the return electrode 144. In the illustrated situation, there is a current path from the transmitting electrode 142 to the return electrode 144 (i.e. the pulmonary vein PV), but there is no current path from the transmitting electrode 140 to the return electrode due to the gap. This may result in the ESU 300 stopping the coagulation procedure.

Finally, the clamp and the tissue coagulation assemblies described above may be combined into an integral unit that cannot be readily separated. For example, the base members may be molded onto the clamp members. Such base members would, for example, extend completely around the each clamp member and/or include portions that are molded into the slots. The base members, clamp members, electrodes, etc. could also be formed as a unitary structure using, for example, insert molding techniques.

III. Exemplary Wettable Structures With Conductive Fibers

As noted above, the resilient members 180 are wettable structures that are configured to be saturated with and retain ionic fluid prior to use so that energy may be transmitted to and from the associated electrodes by way of the ionic fluid. In accordance one of the present inventions, the electrical resistance of such wettable structures may be reduced by adding conductive fibers thereto and, to that end, the resilient members 180b illustrated in FIGS. 17A and 17B include a plurality of conductive fibers 186 in addition to the wettable material. Although the present inventions are not limited to any particular concentration of conductive fibers 186, the conductive fibers will typically occupy less than 5% of the volume of the resilient member 180b.

Wettable structures with conductive fibers may be used in combination with wide variety of devices. By way of example, but not limitation, the resilient members 180b may be carried on the energy transmission devices 126b and 128b illustrated in FIGS. 17A and 17B. The energy transmission devices 126b and 128b may form part of an electrophysiology clamp apparatus that is otherwise identical to the electrophysiology clamp apparatus 100 illustrated in FIG. 1. Another example is the surgical probe 200 described below with reference to FIGS. 19-24.

Although the present inventions are not limited to any particular orientation, the conductive fibers 186 in the illustrated embodiment are parallel to the direction of current flow, which is represented by the arrows CF in FIG. 17A. The current flow direction is generally perpendicular to a flat energy transmission element and radial from a curved energy transmission element, such as the electrodes 140 and 144-in FIGS. 17A and 17B. So arranged, the conductive fibers will be perpendicular to the bottom surface of the wettable material if the resilient member is not curved, or perpendicular to the associated tangent if the resilient member 180b is curved or has been bent over a curved energy transmission element (as it has is in FIGS. 17A and 17B). Orienting the conductive fibers 186 parallel to the current flow direction is considerably more effective from a resistance reduction standpoint than a random orientation. For comparison purposes, conductive fibers that are perpendicular to the current flow direction have almost no influence on electrical impedance until the amount of fibers approaches 30 percent of the volume of the resilient member.

The length of the conductive fibers 186 and their position relative to the electrode are other important considerations. Preferably, the length of the conductive fibers 186 will be at least one-half of the thickness of the resilient wettable structure. Conductive fibers that extend to the bottom surface of the resilient member and are in physical contact with the underlying electrode (as they are in the illustrated embodiment) will have twice the effect on conductance as compared to conductive fibers that are not in physical contact. Moreover, conductive fibers that are spaced more than about 1 fiber radius from the electrode will be essentially disconnected from the electrode.

The fractional increase in electrical conductance of a wettable structure provided with conductive fibers that are parallel to the direction of current flow may be expressed as:

$$[(2)\cdot(\% \text{ Fiber})\cdot(T^2/D^2)]/[-\ln(\% \text{ Fiber})]$$

where % Fiber=the volumetric percentage of fiber in the structure expressed as a decimal (e.g. 1%=0.01), T=the thickness of the wettable structure, D =the average diameter of the conductive fibers.

For example, if metallic fibers that are 0.1 mm in diameter occupy 1 percent of the volume a wettable structure that is 2 mm thick, the fibers would provide an additional conductance of 14-fold compared to that provided by saline alone (i.e. the resistance would be reduced by about 15-fold). Similarly, if carbon fibers that are 0.02 mm in diameter occupy 1 percent of the volume of a wettable structure that is 2 mm thick, the fibers would provide an additional conductance of about 300-fold compared to that provided by saline alone. The resistance of the overall structure would be less than 1 percent of the resistance without the fibers. Even lesser amounts of conductive fibers also provide great benefits. For example, if carbon fibers that are 0.02 mm in diameter occupy 0.1 percent of the volume a wettable structure that is 2 mm thick, the fibers would provide an additional conductance of about 20-fold compared to that provided by saline alone. The resistance of the overall structure would be about 5 percent of the resistance without the fibers. It should also be noted that, in addition to the aforementioned metallic and carbon fibers, fibers formed from electrically conductive plastics may also be used.

The resistivity of the conductive fibers 186 is much lower than the resistivity of ionic fluid (such as saline) and, accordingly, the specific conductivity of the fibers has almost no effect on overall system resistivity within the resilient material. Carbon fiber has a conductivity more than $10^5$ larger than saline, and almost all metals have conductivities $10^8$ or more higher than saline. However, the ratios of the conductivities need only be larger than the $T^2/D^2$ ratio.

One method of manufacturing the wettable resilient member 180b with conductive fibers 186 is illustrated in FIGS. 18A and 18B. First, the conductive fibers 186 are sewn in place into a thin, elongate strip of resilient material 187 such as the aforementioned woven biocompatible material. The conductive fibers 186 may, alternatively, be woven into the strip of resilient material 187. In either case, the conductive fibers 186 are oriented perpendicularly to the longitudinal axis of the strip of resilient material 187. Next, as illustrated in FIG. 18B, the strip of resilient material 187 with the conductive fibers 186 is z-folded back and forth over itself and compressed in the direction of arrow A. This process results in the resilient member 180b with conductive fibers 186 illustrated in FIGS. 17A, 17B, 18C and 18D.

The surgical probe 200 illustrated in FIGS. 19-24 is another example of a device that may include a wettable resilient member with conductive fibers. The surgical probe 200 includes a relatively short shaft 202 with a proximal section 204, which is connected to a handle 206, and a distal section 208, on which coagulation electrodes 210 (or other energy transmission elements) and a tip member 212 are supported. A strain relief device 214 may also be provided. The resilient member 180c illustrated in FIGS. 19, 20 and 23 includes a plurality of conductive fibers 186. The resilient member 180c, which extends around the distal section 208 in the manner illustrated in FIG. 23, is essentially identical to the resilient member 180b, but for the fact that the resilient member 180c extends completely around the underlying electrodes. A barrier member 182c that extends around the resilient member 180c, and is formed from the barrier materials described above, may also be provided if desired.

With respect to the particulars of the exemplary surgical probe 200, the shaft proximal section 204 consists of a hypotube 216, which is either rigid or relatively stiff, and an outer polymer tubing 218 over the hypotube. The shaft proximal section 204 in the illustrated embodiment may be from 4 inches to 18 inches in length and is preferably 6 inches to 8 inches. The shaft distal section 208, which is preferably either malleable, somewhat flexible or some combination thereof, may be from 1 inch to 20 inches in length and is preferably 3 to 5 inches. As used herein the phrase "relatively stiff" means that the shaft (or distal section or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel. In those instances where a malleable shaft proximal portion 204 is desired, the hypotube 216 may be a heat treated malleable hypotube. By selectively heat treating certain portions of the hypotube, one section of the hypotube can be made more malleable than the other. The outer tubing 218 may be formed from Pebax® material, polyurethane, or other suitable materials. Additional information concerning "relatively stiff" shafts is provided in U.S. Pat. No. 6,142,994, which is incorporated herein by reference.

As noted above, the shaft distal section 208 can be either somewhat flexible, in that it will conform to a surface against which it is pressed and then spring back to its original shape when removed from the surface, malleable, or some combination thereof. In the exemplary implementation illustrated in FIGS. 19-24, the distal section 208 includes a malleable proximal portion and a flexible distal portion. Although the relative lengths of the portions may vary to suit particular applications, the malleable proximal portion and a flexible distal portion are equal in length in the illustrated embodiment. Referring more specifically to FIGS. 20, 22 and 23, the exemplary shaft distal section 208 includes an outer member 220 that carries the electrodes 210. The outer member 220 is a flexible tubular structure which has an outer diameter that is, depending on the diameter of the electrodes 210, typically between about 2 mm and about 4 mm. The outer member 220 in the illustrated embodiment, which is intended for use in cardiovascular applications, typically has an outer diameter of about 3 mm. Suitable support structure materials include, for example, flexible biocompatible thermoplastic tubing such as unbraided Pebax® material, polyethylene, or polyurethane tubing.

Turning to the interior of the shaft distal section 208, the exemplary malleable portion includes a mandrel 222 (FIG. 4) made of a suitably malleable material, such as annealed stainless steel or beryllium copper, that may be fixed directly within the distal end of the shaft's hypotube 216 and secured by, for example, soldering, spot welding or adhesives. An insulating sleeve 224, which is preferably formed from Pebax® material, polyurethane, or other suitable materials, is placed over the mandrel 222. With respect to the flexible portion, a spring member 226, which is preferably either a solid flat wire spring (FIG. 5), a round wire, or a three leaf flat wire Nitinol® spring, is connected to the distal end of the mandrel 222 with a crimp tube or other suitable instrumentality. The distal end of the spring member 226 is connected to the tip member 212 by, for example, an adhesive or welding. The tip member 212 is also secured to the distal end of the outer member 220. Other spring members, formed from materials such as 17-7 or carpenter's steel, may also be used. The spring member 226 is also enclosed within the insulating sleeve 224. The spring member 226 may be pre-stressed so that the distal tip is pre-bent into a desired shape. Additional details concerning distal sections that have a malleable proximal portion and a flexible distal portion are provided in U.S. Pat. No. 6,464,700, which is incorporated herein by reference.

In an alternative configuration, the distal section 208 may be formed by a hypotube that is simply a continuation of the shaft hypotube 216 covered by a continuation of the outer tubing 218. However, the distal end hypotube can also be a separate element connected to the shaft hypotube 216, if it is desired that the distal end hypotube have different stiffness (or bending) properties than the shaft hypotube. It should also be noted that the distal section 208 may be made malleable from end to end by eliminating the spring member 226 and extending the malleable mandrel 222 to the tip member 212. Conversely, the distal section 208 may be made flexible from end to end by eliminating the malleable mandrel 222 and extending the spring member 226 from the hypotube 216 to the tip member 212.

The electrodes 210 are preferably wound, spiral closed coils that are preferably about 4 mm to about 20 mm in length and formed from the same materials as the electrodes 140, 142 and 144. In the illustrated embodiment, the surgical probe 200 includes seven (7) electrodes 210 and the electrodes are 12.5 mm in length with 1 mm to 3 mm spacing, which will result the creation of continuous lesion patterns in tissue when coagulation energy is applied simultaneously from adjacent electrodes through tissue to an indifferent electrode. The diameter of the electrodes 210 will typically be about 3 mm. The electrodes 210 may, alternatively, be formed from the other materials and methods discussed above with reference to the electrodes 140, 142 and 144.

A plurality of temperature sensors 228 (FIG. 23), such as thermocouples or thermistors, may be located on, under, abutting the longitudinal end edges of, or in between, the electrodes 210. A reference thermocouple (not shown) may also be provided. In the exemplary implementation, temperature sensors 228 are located at both longitudinal ends of each of the electrodes 210 within a linear channel 230 that is formed in the outer member 220. The linear channel insures that the temperature sensors will all face in the same direction (e.g. facing tissue) and be arranged in linear fashion.

The electrodes 210 are connected to power lines 232 and the temperature sensors 228 are connected to signal lines 234. The power lines 232 may be used to transmit energy from the power supply and control apparatus 300 to the coagulation electrodes 210, while signal lines 234 return temperature information from the temperature sensors 228 to the power supply and control apparatus. The power lines 232 and signal lines 234 extend from the coagulation electrodes 210 and temperature sensors 228 to a connector (such as the exemplary PC board 236 illustrated in FIG. 24) that is carried by the handle 206. The handle 206 also includes a port 238 that is configured to receive a suitable connector, such as the connector 308 from the power supply and control apparatus 300 in the exemplary surgical system 20 illustrated in FIG. 25, for connection to the PC board 238.

IV. Power Control

As noted above, the exemplary ESU 300 supplies and controls power to the tissue coagulation assembly 124 and the surgical probe 200. A suitable ESU is the Model 4810A ESU sold by Boston Scientific Corporation of Natick, Mass., which is capable of supplying and controlling RF power in both bipolar and unipolar modes on an electrode-by-electrode basis. Such electrode-by-electrode power control is sometimes referred to as "multi-channel control." Typically, power will be controlled as a function of the temperature at each electrode in order to insure that tissue is coagulated without over-heating and causing coagulum and charring. With respect to temperature sensing, temperature at the electrodes 140 and 142 on the tissue coagulation assembly 124 is measured by the aforementioned temperatures sensors 170, while temperature at the surgical probe electrodes 210 is measured by the temperature sensors 228. Alternatively, in those instances where temperature sensors are not employed, the respective temperatures at the electrodes may be determined by measuring impedance at each electrode.

Referring to FIG. 1, the exemplary ESU 300 is provided with a power output connector 302 and a pair of return connectors 304 which are respectively configured to be connected to the power and return connectors 164 and 168 on the tissue coagulation assembly 124. As such, the electrodes 140 and 142 and temperature sensors 170 may be connected to the ESU power output connector 302, and the electrode 144 may be connected to the return connector 304. The ESU power output and return connectors 302 and 304 may have different shapes to avoid confusion and the power and return connectors 164 and 168 may be correspondingly shaped. In the exemplary bipolar tissue coagulation assembly 124 illustrated in FIG. 1, for example, the power connector 164 has a generally circular shape corresponding to the ESU power output connector 302 and the return connector 168 has a generally rectangular shape corresponding to the ESU return connector 304.

Turning to FIG. 25, the surgical system 20 includes the surgical probe 200 and the ESU 300. The ESU 300 transmits energy to the electrodes 210 and receives signal from the temperature sensors 228 by way of a cable 306 and a connector 308, which may be connected to the PC board in the surgical probe handle 206 in the manner described above. The exemplary ESU 300 is operable in a bipolar mode, where tissue coagulation energy emitted by one of the electrodes 210 is returned through another, and a unipolar mode, where the tissue coagulation energy emitted by the electrodes is returned through one or more indifferent electrodes 310 that are externally attached to the skin of the patient with a patch, or one or more electrodes (not shown) that are positioned in the blood pool, and a cable 312.

Additional information concerning suitable temperature sensing and RF power supply and control is disclosed in U.S. Pat. Nos. 5,456,682, 5,582,609, 5,755,715 and U.S. Patent Pub. No. 2004/0059325 A1.

V. Stimulation Electrodes and Lesion Confirmation

Electrophysiology devices in accordance with the present inventions may also be provided with stimulation electrodes that are used to stimulate tissue (such as by pacing). The stimulation electrodes may be used to perform a variety of functions before, during and after a lesion formation procedure. For example, and as described in greater detail below, the stimulation electrodes may be used to confirm tissue contact prior to supplying coagulation energy, to evaluate the lesion as the coagulation energy is supplied, and to confirm whether or not a therapeutic lesion has been formed after the coagulation energy has been discontinued. Stimulation energy may be used because non-viable tissue (e.g. coagulated tissue) cannot be stimulated and will not propagate stimulation energy to nearby tissue.

Figure 27:
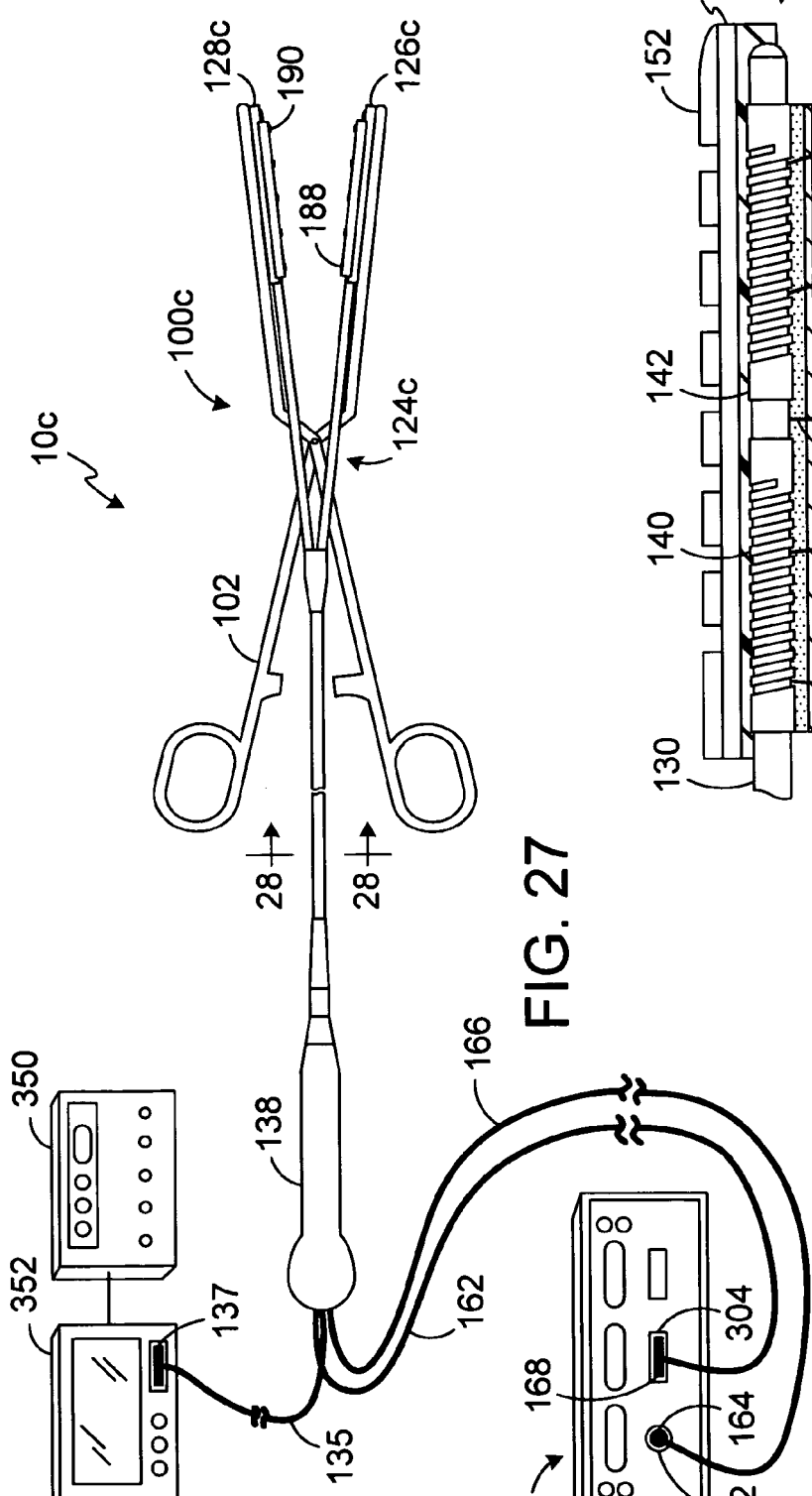
FIG. 27 is a perspective view of a surgical system in accordance with one embodiment of a present invention.
Figure 28:
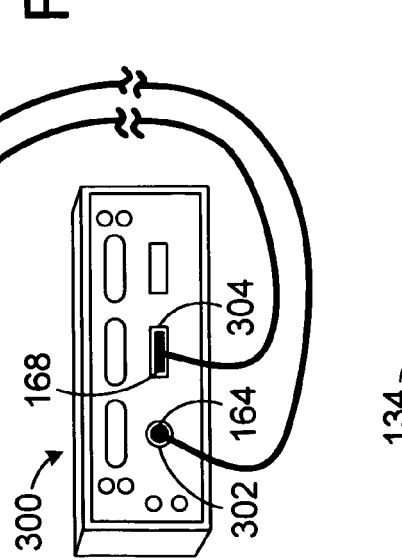
FIG. 28 is a section view taken along line 28-28 in FIG. 27.

To that end, the exemplary electrophysiology system 10c illustrated in FIG. 27 includes an electrophysiology clamp apparatus 100c, the above described ESU 300, a tissue stimulation apparatus 350, and an EP recording apparatus 352. The tissue stimulation apparatus 350 is capable of providing pulses of energy that stimulate (but do not coagulate) tissue. One exemplary tissue stimulation apparatus 350 is a conventional pacing apparatus, such as the Medtronic Model Nos. 5330 and 5388 external pulse generators. The EP recording apparatus 352 is connected to, and directs the tissue stimulation and recording associated with, the tissue stimulation apparatus 350. A suitable EP recording apparatus is the Prucka CardioLab 7000® from GE Medical Systems. Alternatively, the electrophysiology clamp apparatus 100c may be directly connected to the tissue stimulation apparatus 350 or connected to the tissue stimulation apparatus by way of a simple switching box.

It should also be noted that the functionality of the tissue stimulation apparatus 350 may be incorporated into the ESU 300. Here, however, ESU and associated surgical devices should be configured such that coagulation electrodes will only receive coagulation energy and the stimulation electrodes will only receive stimulation energy. Here too, this may be accomplished with different connector configurations. The functionality of the tissue stimulation apparatus 350 and the EP recording apparatus 352 may also be combined into a single device.

With respect to the stimulation energy itself, the power delivered to tissue for stimulation purposes will typically be significantly less than that which would form a transmural or otherwise therapeutic lesion in tissue. An exemplary stimulation energy delivery would consist of two stimulation pulses per second, each pulse being 1 millisecond. The maximum amplitude would typical be 10 mA, which would create 0.5 V, for a total power delivery of 10 µW. As noted above, the amount of power required to coagulate tissue ranges from 5 to 150 W. The amplitude may be increased in those instances where the stimulation pulses are being supplied at the same time as the tissue coagulation energy, as is described below.

Turning to the exemplary electrophysiology clamp apparatus 100c, and as illustrated in FIGS. 26-30, it includes a clamp 102 and a tissue coagulation assembly 124c that is essentially identical to the tissue coagulation assembly 124. Similar elements are used to represent similar elements. Here, however, the first and second energy transmission devices 126c and 128c are provided with stimulation electrodes 188 and 190 in addition to the coagulation electrodes 140-144. The stimulation electrodes 188 and 190 are carried on the energy transmission surfaces 178 of the variable spacing structures 176. Alternatively, the stimulation electrodes 188 and 190 may be located between the resilient member 180 and a barrier member 182 or, in instances where there is no barrier member, simply on the exterior of the resilient member. The stimulation electrodes 188 and 190 may also be used in conjunction with resilient members, such as resilient member 180a, that includes conductive fibers 186. The stimulation electrodes 188 are connected to signal wires 192 and the stimulation electrodes 190 are connected to signal wires 194. The signals wires 192 and 194 are preferably configured such that they will not change the mechanical properties of the resilient material. Suitable signal wires include wires that are 38 gauge or smaller.

The signal wires 192 traverse the resilient material 180 and enter the support structure 130 near the stimulation electrodes 188 (i.e. between the windings of the underlying coagulation electrodes 140 and 142 or between the underlying coagulation electrodes) as shown or, alternatively, just proximal to the underlying coagulation electrodes. The signal wires 194 traverse the resilient material 180 and enter the support structure 132 near the stimulation electrodes 190 (i.e. between the windings of the underlying coagulation electrode 144) as shown or, alternatively, just proximal to the underlying coagulation electrode. The signal lines 192 and 194, which pass through the cable 134, the handle 138, and a cable 135, are connected to the EP recording apparatus 352 by a connector 137.

Figure 26:
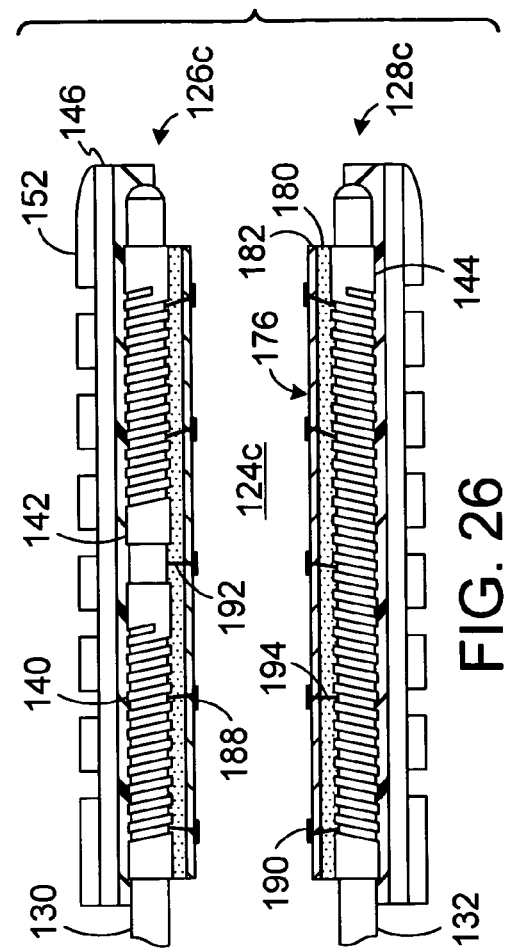
FIG. 26 is a side, partial section view of a tissue coagulation assembly in accordance with one embodiment of a present invention.

Referring to FIGS. 26, 29 and 30, the stimulation electrodes 188 and 190 in the exemplary embodiment are positioned such that they are located between, and aligned with, the tissue coagulation electrodes 140-144. The stimulation electrodes 188 are also preferably aligned with the linear channel 174 (note FIG. 9) so that the stimulation electrodes face the same direction (and the same tissue) as the temperature sensors 170. The location and spacing of the stimulation electrodes 188 on the energy transmission device 126c is the same as it is on the energy transmission device 128c. As such, the clamp apparatus 100c includes pairs of stimulation electrodes 188 and 190 (five pairs in the illustrated embodiment) that are aligned with one another and face one another, when the clamp apparatus grasps a tissue structure, and are aligned with one another and face one another from opposite sides of the tissue structure. In the illustrated embodiment, two pairs of stimulation electrodes 188 and 190 are located between the transmitting electrode 140 and the return electrode 144, two pairs of stimulation electrodes are located between the transmitting electrode 142 and the return electrode, and one pair of stimulation electrodes is located between the small space between transmitting electrodes and the return electrode. The stimulation electrodes 188 and 190 and the coagulation electrodes 140-144 are also located within a common plane.

There are a number of advantages associated with such an arrangement. For example, the placement of tissue stimulation electrodes 188 and 190 on the same surgical device as the tissue coagulation electrodes allows the physician to quickly and easily confirm tissue contact and evaluate the lesion without moving the clamp. Additionally, and as illustrated in FIGS. 31 and 32, the stimulation electrodes 188 and 190 are located between the energy transmitting portions of the energy transmission devices 126c and 128c and are also in the current path CP between the energy transmission devices (which is shown by the dash lines in FIG. 31). This arrangement provides more accurate information when the stimulation electrodes 188 and 190 are being used to confirm tissue contact prior to supplying coagulation energy because the stimulation electrodes are in contact with the portions of the tissue structure through which current will be transmitted, as opposed to being in contact with tissue that is merely close to the current path. The location of the stimulation electrodes 188 and 190 also provides more accurate information concerning the lesion itself during and after the tissue coagulation procedure because the stimulation electrodes are in direct contact with the coagulated tissue CT (FIG. 32). The assessment of the lesion is localized (i.e. the assessment is made directly on the target tissue within the current path) and, therefore, facilitates lesion assessment processes that are easier to implement than those which involve stimulating tissue on one side of a lesion and sensing tissue on the other. Here, the assessment is simply whether or not stimulation of the tissue adjacent to the lesion occurs, as opposed to an assessment of the propagation delay between the stimulation pulse on one side of the lesion and the stimulation on the other.

With respect to the specific methods by which tissue contact may be confirmed after the physician has positioned the energy transmission devices 126c and 128c on opposite sides of a tissue structure, the stimulation electrodes 188 and 190 may be used to supply pulses of stimulation energy (sometimes referred to as "pacing" pulses) to the tissue in the current path CP between the energy transmission devices. The stimulation energy will preferably be supplied in bipolar fashion to a single stimulation electrode pair. The physician will then monitor the adjacent tissue, either visually or with a monitor such as an ECG to determine whether that tissue was stimulated. In the context of the treatment of atrial fibrillation, for example, the procedure may be performed after the energy transmission devices 126c and 128c are epicardially positioned about one or more of the pulmonary veins. If the stimulation energy stimulates (or "paces") the adjacent tissue (here, the left atrium), the physician will know that proper contact has been achieved for the associated portions of the energy transmission devices 126c and 128c. This process may be sequentially repeated with the other stimulation electrode pairs to insure proper tissue contact with the other portions of the energy transmission devices 126c and 128c. Thereafter, and without moving the electrophysiology clamp apparatus 100c, tissue coagulation energy may be applied to the tissue in the current path CP with the electrodes 140-144 to form a lesion.

As noted above, stimulation energy may also be used while the tissue coagulation energy is being supplied in order to determine when a transmural lesion has been completely formed. Here, stimulation energy pulses may be supplied by the electrode pairs to the tissue in the current path CP in the manner described above. The tissue adjacent to the current path will be monitored, either visually or with an ECG, to determine when the adjacent tissue is no longer being stimulated. The supply of tissue coagulation energy may be discontinued in response to such a determination. For example, if the ESU 300 is programmed to supply coagulation energy for 30 seconds, the supply of energy could end after 25 seconds if the lesion is completed earlier than was anticipated, as determined by the inability to stimulate the adjacent tissue. This may be accomplished either manually, or automatically, if the ECG is connected to the ESU 300.

It should be noted that tissue becomes non-stimulatable before it is irreversibly coagulated or otherwise irreversibly damaged. Accordingly, tissue coagulation energy should continue to be supplied for a few seconds after the adjacent tissue ceases to be stimulated by stimulation energy pulses (i.e. there should be a brief delay before the coagulation energy is discontinued). It should also be noted that while coagulation energy is being supplied by the electrodes 140-144, the stimulation energy should be supplied at a significantly higher amplitude (e.g. 5 times higher) than it would be before or after the coagulation procedure because tissue that is heated is harder to stimulate. For example, if 4 mA pulses are suitable before and after the coagulation procedure, then 20 mA pulses should be used during the coagulation procedure.

Finally, stimulation energy may be supplied after tissue coagulation energy has been discontinued, either at the end of the pre-programmed period or based on the sensed completion of the lesion, in order to determine whether a transmural lesion has been formed. Without moving the clamp, stimulation energy pulses may be supplied by the electrode pairs to the tissue in the current path CP in the manner described above. The adjacent tissue will be monitored, either visually or with the ECG, to determine whether the adjacent tissue can be stimulated. If not, the physician may assume that a transmural lesion has been formed. In those instances where the lesion is incomplete, the individual stimulation electrode pairs may be used to determine where the gap (i.e. the portion of the lesion that is not transmural) is located. Additional coagulation energy may then be supplied as necessary to complete the lesion. Of course, it may be the case that the entire lesion is not transmural, which would require the coagulation procedure to be at least partially repeated.

With respect to sizes and materials, the stimulation electrodes 188 and 190 are relatively small (i.e. too small to form transmural myocardial lesions), solid, low profile devices. Suitable surface are sizes are about 0.2 mm$^2$ to 10 mm$^2$, and suitable thicknesses are about 0.01 mm to 0.5 mm. The electrodes in the illustrated embodiment are about 1 mm$^2$ and about 0.1 mm thick. Suitable materials include platinum, platinum iridium, stainless steel, gold, silver-silver chloride or other non-toxic metals. Stimulation electrodes may also be formed by coating a conductive material onto the variable spacing structures 176 or other underlying structure using conventional coating techniques or an IBAD process. Suitable conductive materials include platinum-iridium and gold. An undercoating of nickel, silver or titanium may be applied to improve adherence. Conductive ink compounds, such as silver-based flexible adhesive conductive ink (polyurethane binder) or metal-based adhesive conductive inks (e.g. platinum, gold, or copper based) may also be pad printed in place. With respect to assembly, the signal wires 190 and 192 may be welded or soldered to solid stimulation electrodes prior to assembly, while coated/printed electrodes may be formed onto the ends of signal wires that are already in place.

Surgical probes may also be provided with stimulation electrodes. The exemplary surgical probe 200a illustrated in FIGS. 33-36 is essentially identical to the surgical probe 200 and similar elements are represented by similar reference numerals. Here, however, the distal section 208a includes a plurality of the above-described stimulation electrodes 188. The stimulation electrodes 188 are arranged such that a pair of stimulation electrodes is aligned with each of the seven coagulation electrodes 210. Signal wires 192, which are connected to the stimulation electrodes 188 in the manner described above, extend through a cable 240 to a connector 242. The handle 206a includes an aperture 244 for the cable 240.

The surgical probe 200a may be incorporated into the exemplary electrophysiology system 20a (FIG. 33), which also includes the aforementioned ESU 300, tissue stimulation apparatus 350, and EP recording apparatus 352. There are a number of advantages associated with such as system. Most notably, positioning the tissue stimulation electrodes 188 on the same surgical device as the tissue coagulation electrodes 210 allows the physician to quickly and easily confirm tissue contact and evaluate the lesion without moving the probe. Typically, this will involve providing monopolar stimulation pulses from the pairs of stimulation electrodes 188 that are associated with the coagulation electrodes 210 that will be forming the lesion.

Figure 37:
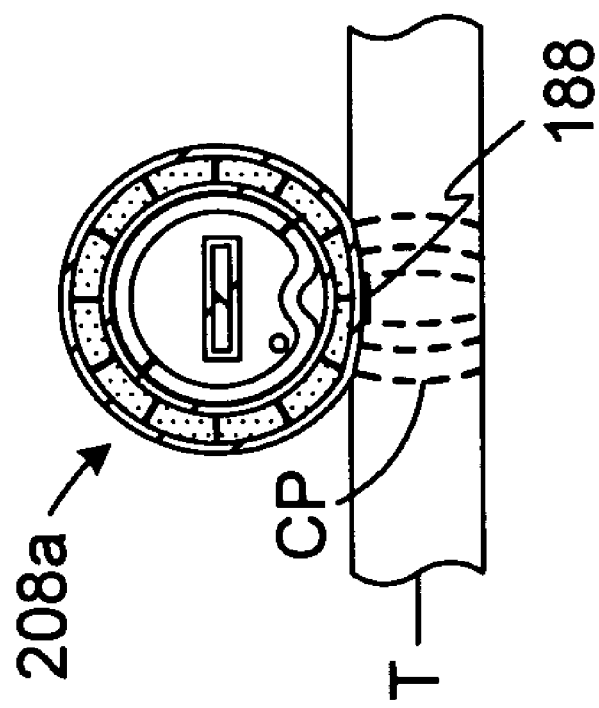
FIG. 37 is a section view of a portion of a lesion formation process in accordance with one embodiment of a present invention.

With respect to tissue contact, and referring to FIG. 37, the stimulation electrode pairs may be used to supply pulses of stimulation energy to the tissue in the current path CP associated with one of the coagulation electrodes 210. The physician will then monitor the adjacent tissue in the tissue structure T, either visually or with an ECG, to determine whether that tissue was stimulated. This process may be sequentially repeated with the other stimulation electrode pairs in order to insure proper tissue contact with the applicable portions of the surgical probe distal section 208a. Thereafter, and without moving the distal section, tissue coagulation energy may be applied to the tissue in the current path CP with the electrodes 210 to form a lesion.

Figure 38:
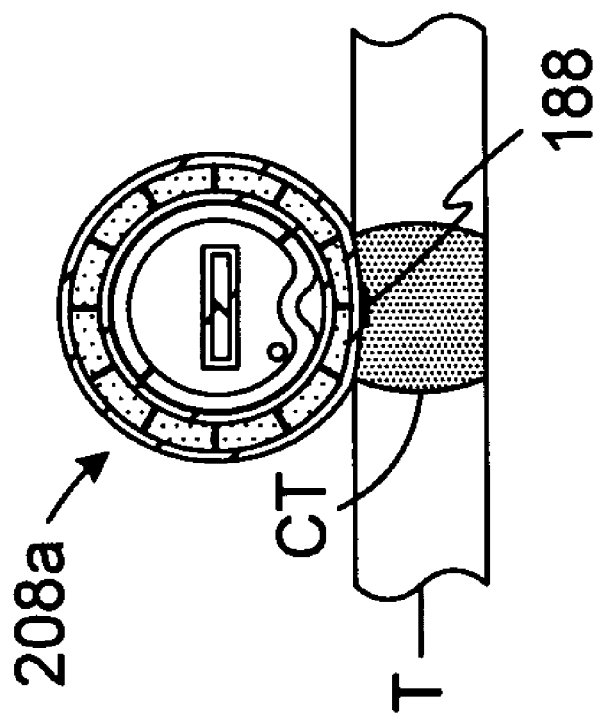
FIG. 38 is a section view of a portion of a lesion formation process in accordance with one embodiment of a present invention.

Turning to FIG. 38, the stimulation electrodes 188 may also be used to determine lesion depth and, correspondingly, whether or not a lesion is transmural at various points along the length of the lesion. Stimulation energy may be used to determine lesion depth because non-viable tissue (e.g. coagulated tissue) cannot be stimulated and will not propagate stimulation energy to nearby tissue. As such, when the application of stimulation energy that should stimulate tissue at a known depth fails to do so, and that depth is greater than or equal to the thickness of the body structure, it may be inferred that a transmural lesion has been formed. Preferably, the stimulation electrodes will be used on a coagulation electrode-by-coagulation electrode basis both during and before the coagulation process in the manner described above.

In the context of lesions formed within the heart, for example, localized current densities must exceed about 2 mA/cm$^2$ to stimulate heart tissue. With respect to current transmitted from an electrode to tissue, the current density is about $1/2\pi r^2$, where r is the distance from the electrode. Thus, a 1 mA stimulation pulse will typically stimulate viable tissue that is no more than about 2.8 mm from the electrode, a 2 mA stimulation pulse will typically stimulate viable tissue that is no more than about 4.0 mm from the electrode, a 10 mA stimulation pulse will typically stimulate viable tissue that is no more than about 9.0 mm from the electrode, and a 20 mA stimulation pulse will typically stimulate viable tissue that is no more than about 13.0 mm from the electrode. The left atrium is, for example, about 3 mm thick and accordingly, failure to stimulate with a 2 mA stimulation pulse indicates that a transmural lesion has been formed in the vicinity of the stimulation electrode. As noted above, these values should be substantially increased (e.g. by a factor of five) when the stimulation pulses are being supplied at the same time as the coagulation energy.

It should also be noted that there are a number of advantages associated with location of the stimulation electrodes 188 relative to the coagulation electrodes 210. For example, the stimulation electrodes 188 are positioned between the coagulation electrodes 210 and target tissue, as opposed to being positioned on the distal section outer member 220 between the coagulation electrodes. As such, the stimulation electrodes 188 are in the current path of each coagulation electrode 210, as opposed to being in between the current paths the coagulation electrodes.

Although the inventions disclosed herein have been described in terms of the preferred embodiments above, numerous modifications and/or additions to the above-described preferred embodiments would be readily apparent to one skilled in the art. By way of example, but not limitation, tissue coagulation assemblies in accordance with the present inventions may be configured such that only one of the energy transmission devices includes a variable spacing device and/or such that the energy transmission devices are otherwise not identical. It is intended that the scope of the present inventions extend to all such modifications and/or additions and that the scope of the present inventions is limited solely by the claims set forth below.

I claim:

1. A tissue ablation apparatus, comprising:
   a support structure;
   an energy transmission element carried on an outer portion of the support structure and configured for transmitting ablative energy;
   a structure carried on an outer portion of the energy transmission element, the structure including a resilient member and a plurality of conductive fibers, the resilient member being configured to retain ionic fluid; and a porous barrier member carried on an outer portion of the resilient member to secure the resilient member against the energy transmission element, the porous barrier member being configured to retain ionic fluid and having an energy transmission surface for contacting tissue, wherein ablative energy is transmitted from the energy transmission element and to tissue through ionic fluid retained by the resilient member and the porous barrier member.

2. An apparatus as claimed in claim 1, wherein the support structure is configured to be removably secured to a clamp.

3. The apparatus of claim 2, further comprising a mounting device comprising a base member, the base member defining a groove that receives the support structure and the energy transmission element and being configured to be removably secured to the clamp.

4. The apparatus of claim 3, the base member comprising a connector configured to engage a slot defined by the clamp to removably secure the base member to the clamp.

5. The apparatus of claim 3, the porous barrier member extending between opposite sides of the base member.

6. An apparatus as claimed in claim 1, wherein the support structure comprises a surgical probe shaft.

7. An apparatus as claimed in claim 1, wherein the energy transmission element comprises an electrode.

8. An apparatus as claimed in claim 1, wherein the resilient member comprises woven material.

9. An apparatus as claimed in claim 1, wherein the conductive fibers comprise at least one of metallic fibers, carbon fibers, and conductive plastic fibers.

10. An apparatus as claimed in claim 1, wherein the energy transmission element defines a current flow direction and the conductive fibers are substantially parallel to the current flow direction.

11. An apparatus as claimed in claim 1, wherein the conductive fibers are in physical contact with the energy transmission element.

12. An apparatus as claimed in claim 1, wherein the resilient member defines a thickness and the conductive fibers define respective lengths that are at least one-half of the resilient member thickness.

13. An apparatus as claimed in claim 1, wherein the structure defines a volume and the conductive fibers occupy less than about 5% of the structure volume.

14. An apparatus as claimed in claim 1, wherein the plurality of conductive fibers are within the resilient member.

15. The apparatus of claim 1, wherein the porous barrier member is a biocompatible fabric.

16. The apparatus of claim 1, wherein the energy transmission element encircles the support structure, and the resilient member partially encircles the energy transmission element.

17. The apparatus of claim 16, wherein the porous barrier member partially encircles the structure including the resilient member and the plurality of conductive fibers.

18. The apparatus of claim 1, wherein the porous barrier member is carried on the outer portion of the resilient member to secure the resilient member against the energy transmission element.

19. An apparatus for use with an energy transmission element of a probe for ablating tissue, comprising:
    an energy transmission element operable to transmit ablative energy;
    a resilient, wettable structure carried on an outer surface of the energy transmission element and configured to be saturated with and retain ionic fluid;
    a plurality of conductive fibers within the resilient, wettable structure; and
    a porous barrier member positioned over an outer portion of the resilient, wettable structure to secure the resilient, wettable structure against the energy transmission element, the porous barrier member being configured to retain ionic fluid and having an energy transmission surface for contacting tissue, wherein ablative energy is transmitted through ionic fluid retained by the resilient, wettable structure and the porous barrier member.

20. An apparatus as claimed in claim 19, wherein the resilient, wettable structure comprises woven material.

21. An apparatus as claimed in claim 19, wherein the conductive fibers comprise at least one of metallic fibers, carbon fibers, and conductive plastic fibers.

22. An apparatus as claimed in claim 19, wherein the resilient, wettable structure defines a first surface and a second surface and the conductive fibers extend to at least one of the first and second surfaces.

23. An apparatus as claimed in claim 19, wherein the resilient, wettable structure defines a bottom surface and the conductive fibers are substantially perpendicular to the bottom surface.

24. An apparatus as claimed in claim 19, wherein the resilient, wettable structure defines a thickness and the conductive fibers define respective lengths that are at least one-half of the resilient, wettable structure thickness.

25. An apparatus as claimed in claim 19, wherein the apparatus defines a volume and the conductive fibers occupy less than about 5% of the apparatus volume.

26. The apparatus of claim 19, wherein the porous barrier member is a biocompatible fabric.

27. An apparatus for use with an energy transmission element for ablating tissue, comprising:
    an energy transmission element operable to transmit ablative energy;
    a resilient, wettable structure carried on an outer surface of the energy transmission element and configured to be saturated with and retain ionic fluid such that the resilient, wettable structure defines a saturated conductance when saturated with ionic fluid;
    means, within the resilient, wettable structure, for increasing the saturated conductance of the resilient, wettable structure; and
    a porous barrier member positioned over an outer portion of the resilient, wettable structure to secure the resilient, wettable structure against the energy transmission element, the porous barrier member being configured to retain ionic fluid and having an energy transmission surface for contacting tissue, wherein ablative energy is transmitted to tissue through ionic fluid retained by the resilient, wettable structure and the porous barrier member.

28. An apparatus as claimed in claim 27, wherein the resilient, wettable structure comprises woven material.

29. The apparatus of claim 27, wherein the porous barrier member is a biocompatible fabric.

* * * * *